United States Patent
Belobraydich et al.

(10) Patent No.: US 10,145,967 B2
(45) Date of Patent: Dec. 4, 2018

(54) SYSTEMS AND METHODS FOR RADIATION DETECTION WITH IMPROVED EVENT TYPE DISCRIMINATION

(71) Applicant: PerkinElmer Health Sciences, Inc., Waltham, MA (US)

(72) Inventors: Michael Belobraydich, Plainfield, IL (US); Richard Harazin, Lombard, IL (US)

(73) Assignee: PERKINELMER HEALTH SCIENCES, INC., Waltham, MA (US)

(*) Notice: Subject to any disclaimer, the term of this patent is extended or adjusted under 35 U.S.C. 154(b) by 105 days.

(21) Appl. No.: 15/337,885

(22) Filed: Oct. 28, 2016

(65) Prior Publication Data

US 2018/0113223 A1  Apr. 26, 2018

Related U.S. Application Data

(60) Provisional application No. 62/411,448, filed on Oct. 21, 2016.

(51) Int. Cl.
  *G01T 1/20* (2006.01)
  *G01T 1/208* (2006.01)
  (Continued)

(52) U.S. Cl.
  CPC ......... *G01T 1/208* (2013.01); *G01N 15/1429* (2013.01); *G01T 1/178* (2013.01); *G01T 1/204* (2013.01)

(58) Field of Classification Search
  CPC .............. G01T 1/00; G01T 1/20; G01T 1/208
  See application file for complete search history.

(56) References Cited

U.S. PATENT DOCUMENTS

| 3,818,356 A | 6/1974 | Kinbara |
| 3,988,586 A | 10/1976 | Stuart et al. |

(Continued)

FOREIGN PATENT DOCUMENTS

| GB | 1497367 A | 1/1978 |
| GB | 2484393 A | 4/2012 |

(Continued)

OTHER PUBLICATIONS

Bower et al., "Alpha-beta discrimination liquid scintillation counting for uranium and its daughters," 1994, Journal of Radioanalytical and Nuclear Chemistry, Articles, vol. 181, No. 1, pp. 97-107.*

(Continued)

*Primary Examiner* — Kiho Kim
(74) *Attorney, Agent, or Firm* — Choate, Hall & Stewart, LLP; William R. Haulbrook; Ronen Adato

(57) ABSTRACT

Described herein are radiation detection systems and methods that provide improved discrimination between different types of radioactive events. The use of multiple discriminator settings based on pulse curve shape, rather than a single setting, is surprisingly found to improve discrimination between alpha and beta events. Results demonstrate significantly lowered % spill with minimal loss of efficiency due to the enhanced discrimination. These systems and methods are particularly important in the detection of extremely low-level alpha and beta events, and in the identification and quantification of isotopes with difficult-to-distinguish pulse shapes.

22 Claims, 13 Drawing Sheets

(51) Int. Cl.
*G01N 15/14* (2006.01)
*G01T 1/204* (2006.01)
*G01T 1/178* (2006.01)

(56) References Cited

U.S. PATENT DOCUMENTS

| | | | |
|---|---|---|---|
| 4,651,006 A | 3/1987 | Valenta | |
| 4,742,226 A * | 5/1988 | De Filippis | G01T 1/2045 250/328 |
| 5,317,158 A | 5/1994 | McElhaney et al. | |
| 5,399,869 A * | 3/1995 | Usuda | G01T 1/2008 250/367 |
| 5,483,070 A | 1/1996 | Valenta | |
| 5,489,775 A * | 2/1996 | Viera | G01T 1/178 250/252.1 |
| 6,392,236 B1 * | 5/2002 | Maekawa | G01T 1/2008 250/369 |
| 8,796,632 B2 | 8/2014 | Aspinall et al. | |
| 9,297,909 B2 | 3/2016 | Harazin | |
| 2004/0206909 A1 | 10/2004 | Izumi et al. | |
| 2004/0262530 A1 | 12/2004 | Reber et al. | |
| 2006/0081786 A1 * | 4/2006 | Berthold | G01T 1/20 250/370.11 |
| 2007/0051893 A1 | 3/2007 | Matsumoto | |
| 2007/0290136 A1 | 12/2007 | Ivan | |
| 2009/0039271 A1 * | 2/2009 | Farsoni | G01T 1/202 250/367 |
| 2012/0080598 A1 | 4/2012 | Aspinall et al. | |
| 2013/0275087 A1 * | 10/2013 | Scott | G01T 1/17 702/189 |
| 2013/0277565 A1 | 10/2013 | Bogorodzki et al. | |
| 2015/0021489 A1 | 1/2015 | Bogorodzki et al. | |
| 2015/0301194 A1 | 10/2015 | Harazin | |
| 2015/0323682 A1 | 11/2015 | Yang et al. | |

FOREIGN PATENT DOCUMENTS

| | | |
|---|---|---|
| JP | 2004163352 A | 6/2004 |
| WO | WO-2015/160480 A1 | 10/2015 |
| WO | WO-2015/0171919 A1 | 11/2015 |

OTHER PUBLICATIONS

Perkinelmer, Scintillating Results at Your Lowest Concentrations, PerkinElmer, Inc., 12 Pages (2015).
Edler, R. et al., Basics of alpha/beta-discrimination for liquid scintillation counting, (2010) Retrieved from the Internet: URL:http://www.perkinelmer.co.jp/Portals/0/resource/data/pdf/ApplicationNotes/LS_AN_009379_01.pdf [retrieved on Jun. 29, 2017].
EG&G Wallac, Quantulus 1220 Instrument Manual, Wallac Oy, pp. 21-24, Feb. 1999.
International Search Report, PCT/US2016/059508, 4 pages, dated Jul. 14, 2017.
Perkinelmer Life Sciences, Instrument Manual, Wallac 1220 Quantulus, Ultra Low Level Liquid Scintillation Spectrometer, 210 pages (2002).
Thomson, J., Use and Preparation of Quench Curves in Liquid Scintillation Counting, Packard BioScience, Liquid Scintillation Counting, Application Note LSC-007, pp. 1-6 (2001).
University of Wisconsin, Milwaukee Environmental Health, Safety and Risk Management Radiation Safety Program, Liquid Scintillation Counting, 14 pages (1999).
Written Opinion, PCT/US2016/059508, 9 pages, dated Jul. 14, 2017.

* cited by examiner

SYSTEMS AND METHODS FOR RADIATION DETECTION WITH IMPROVED EVENT TYPE DISCRIMINATION

RELATED APPLICATION

The present application claims priority to and the benefit of, and incorporates herein by reference in its entirety, U.S. Provisional Patent Application No. 62/411,448, filed Oct. 21, 2016.

TECHNICAL FIELD

This invention relates generally to systems and methods for radiation detection in test samples. More particularly, in certain embodiments, the invention relates to systems (e.g., a liquid scintillation counter) that provide improved discrimination between different kinds of radioactive events (e.g., alpha v. beta) in a test sample.

BACKGROUND

Radionuclides that are present in a sample may be identified and quantified by detecting and analyzing the radiation emitted from the sample. This is important in many contexts, such as the detection of tritium, radon, radium, and uranium in drinking water; the detection of strontium in food; the detection of $^{14}C$ in food, alcohol, and biofuels; evaluations of tritium and $^{14}C$ emissions from nuclear power plants; the monitoring of radioactivity during decommissioning of nuclear reactors; tracer measurements in oil exploration; adsorption, distribution, metabolism, and excretion (ADME) studies; the detection of radionuclides in biological samples (e.g., identification of viable drug pathways in drug development); and radiocarbon dating of archaeological samples, as well as many other biological and environmental contexts.

There are a variety of systems and analytical techniques available for detection of events caused by the radioactive decay of radionuclides in a sample. Where the sample contains a plurality of radionuclides that emit different kinds of radiation (e.g., both alpha and beta emitters), or where a sample contains a radionuclide of unknown type, it is important to be able to determine whether a detected radioactive event is caused by alpha, beta, or gamma radiation.

For example, in liquid scintillation counting, a sample material containing one or more radionuclides to be identified is mixed with a solvent capable of dissolving the sample material, along with a scintillator (e.g., a fluor). A vial of the resulting cocktail is placed in a detector comprising one or more photomultiplier tubes. When the radionuclide(s) undergo radioactive decay, the emitted decay energy causes excitation of the scintillator and release of UV light, which is detected. The intensity of the light is a function of the decay energy, and the shape of the detected pulse can be used to distinguish between different kinds of radioactive events, e.g., alpha, beta, or gamma radiation. The detector produces a pulse signal corresponding to each of a plurality of radioactive events detected in the test sample. The identity and/or quantity of the radionuclide can then be determined.

It is recognized that pulse shape may be indicative of various kinds of radioactive events. For example, a pulse of light detected by a liquid scintillation counter (LSC) can be classified as having been caused by either an emitted beta particle or an alpha particle based on its pulse shape. FIG. 1 is a plot showing normalized light intensity as a function of time. The alpha pulse has a longer tail (longer decay period) than the beta pulse. By using appropriate calibration samples according to the expected radionuclides in a test sample, a discriminator can be derived to classify a given radioactive event in the test sample as either alpha or beta radiation.

Similarly, U.S. Patent Application Publication US 2004/0262530 presents a technique for discrimination between pulses produced by neutrons and gamma rays based on pulse shape.

However, current discrimination techniques suffer from alpha/beta misclassification (spill), particularly when used in the detection of extremely low-level alpha and beta events, and when used to identify isotopes with difficult-to-distinguish pulse shapes, such as Strontium-90.

Thus, there is a need for improved systems and methods for discrimination between different kinds of radioactive events (e.g., alpha v. beta) in a test sample.

SUMMARY OF THE INVENTION

Presented herein are radiation detection systems and methods that provide for improved discrimination between different types of radioactive events. The use of multiple discriminator settings based on pulse curve shape, rather than a single setting, is surprisingly found to improve discrimination between alpha and beta events. Results demonstrate significantly lowered % spill with minimal loss of efficiency due to the enhanced discrimination. These systems and methods are particularly important in the detection of extremely low-level alpha and beta events, and in the identification and quantification of isotopes with difficult-to-distinguish pulse shapes.

Furthermore, systems and methods are presented herein that allow a user to adjust the multiple discriminator settings, e.g., via an interactive histogram display, permitting self-selection of the trade-off between discrimination accuracy and efficiency. In other embodiments, the systems and methods automatically determine the multiple discriminator settings based on a figure of merit that minimizes misclassification error and maximizes efficiency.

In one aspect, the invention is directed to a method for quantifying two or more kinds of radionuclides present in a test sample, the method comprising: for each of a plurality of finite detected radioactive events in the test sample, obtaining, by a processor of a computing device, a measure of pulse shape, where the measure is a function of pulse intensity and pulse duration; sorting, by the processor, each of the finite detected radioactive events according to its measure of pulse shape into one of at least three categories using distinct first and second discriminator settings, where the event is identified as originating from a first kind of radionuclide if its pulse shape has a value below the first discriminator setting, the event is identified as originating from a second kind of radionuclide if its pulse shape has a value above the second discriminator setting, and the event is identified as indeterminate if its pulse shape has a value between the first and second-discriminator settings; and displaying, by the processor, a measure of the first kind of radionuclide and a measure of the second kind of radionuclide.

In certain embodiments, the two or more kinds of radionuclides comprise a beta emitter and an alpha emitter.

In certain embodiments, each of the plurality of finite detected radioactive events has an associated signal of detected light intensity measured as a function of time by a liquid scintillation counter from which the measure of pulse shape is determined.

In certain embodiments, the measure of pulse shape is or is a function of a measure of pulse or tail area divided by pulse amplitude.

In certain embodiments, the event is identified as originating from a beta emitter if its pulse shape has a value below the first discriminator setting and the event is identified as originating from an alpha emitter if its pulse shape has a value above the second discriminator setting, where the first discriminator setting is lower than the second discriminator setting. In certain embodiments, the sorted events include a non-zero number of events in each of three categories—events originating from the first kind of radionuclide, events originating from the second kind of radionuclide, and indeterminate events.

In certain embodiments, the measure of the first kind of radionuclide is or is a function of a sum of sorted events having a pulse shape value below the first discriminator setting, and the measure of the second kind of radionuclide is or is a function of a sum of sorted events having a pulse shape value above the second discriminator setting.

In another aspect, the invention is directed to a method for applying discriminator settings in the quantification of radionuclides present in a test sample comprising at least a first and second radionuclide that are of different kinds, the method comprising: receiving, by a processor of a computing device, data corresponding to a measure of pulse shape for each of a plurality of finite detected radioactive events in a first calibration sample comprising a first calibration radionuclide that is the same kind of emitter as and is or is similar to the first radionuclide in the test sample; receiving, by the processor, data corresponding to a measure of pulse shape for each of a plurality of finite detected radioactive events in a second calibration sample comprising a second calibration radionuclide that is the same kind of emitter as and is or is similar to the second radionuclide in the test sample; displaying, by the processor, a graphical representation of differentiated radioactive events corresponding to the first and second calibration samples as a function of corresponding measure of pulse shape; displaying, by the processor, a graphical user interface element allowing adjustment of one or both of a first discriminator setting, and a second discriminator setting, and where an event is identified as originating from the first radionuclide if its pulse shape value is below the first discriminator setting, the event is identified as originating from the second radionuclide if its pulse shape value is above the second discriminator setting, and the event is identified as indeterminate if its pulse shape value is between the first and second discriminator settings; receiving, by the processor, a selection by a user of a setting of the graphical user interface element defining the first and second discriminator settings; determining and displaying, by the processor, a measure of spill and/or a measure of efficiency for each of the first and second calibration radionuclides given the user-selected setting of the graphical user interface element; receiving, by the processor, an adjusted setting of the graphical user interface element corresponding to one or both of an adjusted first discriminator setting, and an adjusted second discriminator setting; determining and displaying, by the processor, a measure of spill and/or a measure of efficiency for each of the first and second calibration radionuclides according to the adjusted setting of the graphical user interface element; obtaining, by the processor, for each of a plurality of finite detected radioactive events in the test sample, a measure of pulse shape; sorting, by the processor, each of the finite detected radioactive events in the test sample according to its measure of pulse shape using the adjusted setting of the graphical user interface element; and displaying, by the processor, a measure of the first radionuclide in the test sample and the second radionuclide in the test sample according to the adjusted setting of the graphical user interface element.

In certain embodiments, the first radionuclide in the test sample is a beta emitter and the second radionuclide in the test sample is an alpha emitter. In certain embodiments, each of the plurality of finite detected radioactive events in at least one of (i) the first calibration sample, (ii) the second calibration sample, and (iii) the test sample has an associated signal of detected light intensity measured as a function of time by a liquid scintillation counter from which the measure of pulse shape is determined.

In certain embodiments, the first calibration sample does not comprise any radionuclide other than the first calibration radionuclide and/or wherein the second calibration sample does not comprise any radionuclide other than the second calibration radionuclide.

In certain embodiments, the measure of pulse shape is or is a function of a measure of pulse or tail area divided by pulse amplitude.

In certain embodiments the graphical representation of differentiated radioactive events comprises a histogram and/or a computation of % spill.

In certain embodiments the adjusted setting is a user-adjusted setting.

In certain embodiments the method comprises sorting, by the processor, each of the finite detected radioactive events in the test sample according to its measure of pulse shape using the adjusted first discriminator setting and the adjusted second discriminator setting. In certain embodiments, the method comprises sorting, by the processor, each of the finite detected radioactive events according to its measure of pulse shape into one of at least three categories using distinct first and second discriminator settings, where the event is identified as originating from a first kind of radionuclide if its pulse shape has a value below the adjusted first discriminator setting, the event is identified as originating from a second kind of radionuclide if its pulse shape has a value above the adjusted second discriminator setting, and the event is identified as indeterminate if its pulse shape has a value between the adjusted first and the adjusted second discriminator settings.

In certain embodiments, the event is identified as originating from a beta emitter if its pulse shape has a value below the adjusted first discriminator setting and the event is identified as originating from an alpha emitter if its pulse shape has a value above the adjusted second discriminator setting, where the adjusted first discriminator setting is lower than the adjusted second discriminator setting. In certain embodiments, the sorted events include a non-zero number of events in each of three categories—events originating from the first kind of radionuclide, events originating from the second kind of radionuclide, and indeterminate events.

In certain embodiments, the measure of the first kind of radionuclide in the test sample is or is a function of a sum of sorted events having a pulse shape value below the adjusted first discriminator setting, and the measure of the second kind of radionuclide in the test sample is or is a function of a sum of sorted events having a pulse shape value above the adjusted second discriminator setting.

In another aspect, the invention is directed to a method for automatically optimizing discriminator settings in the quantification of radionuclides present in a test sample comprising at least a first and second radionuclide that are of different kinds, the method comprising: receiving, by a processor of a computing device, data corresponding to a measure of pulse shape for each of a plurality of finite detected radioactive events in a first calibration sample comprising a first calibration radionuclide that is the same kind of emitter as (e.g., a beta emitter) and is or is similar to the first radionuclide in the test sample; receiving, by the processor, data corresponding to a measure of pulse shape for each of a plurality of finite detected radioactive events in a second calibration sample comprising a second calibration radionuclide that is the same kind of emitter as and is or is similar to the second radionuclide in the test sample; for each of a plurality of settings of both of a first discriminator setting and a second discriminator setting (different from the first discriminator setting), determining, by the processor, for each of the first and second calibration radionuclides: (i) a measure of spill and (ii) a measure of efficiency, where an event is identified as originating from the first calibration radionuclide if its pulse shape value is below the first discriminator setting, the event is identified as originating from the second calibration radionuclide if its pulse shape value is above the second discriminator setting, and the event is identified as indeterminate if its pulse shape value is between the first and second discriminator settings; computing, by the processor, a figure of merit (FOM) corresponding to each of the plurality of settings of the first discriminator setting and the second discriminator setting, where the FOM is a function of spill and efficiency; determining, by the processor, an accepted setting of the first discriminator setting and the second discriminator setting that produces an acceptably high FOM; obtaining, by the processor, for each of a plurality of finite detected radioactive events in the test sample, a measure of pulse shape; sorting, by the processor, each of the finite detected radioactive events in the test sample according to its measure of pulse shape using the accepted setting of the first discriminator setting and the second discriminator setting; and displaying, by the processor, a measure of the first radionuclide in the test sample and the second radionuclide in the test sample according to the accepted setting of the first discriminator setting and the second discriminator setting.

In certain embodiments, the first radionuclide in the test sample is a beta emitter and the second radionuclide in the test sample is an alpha emitter.

In certain embodiments, each of the plurality of finite detected radioactive events in at least one of (i) the first calibration sample, (ii) the second calibration sample, and (iii) the test sample has an associated signal of detected light intensity measured as a function of time by a liquid scintillation counter from which the measure of pulse shape is determined.

In certain embodiments, the first calibration sample does not comprise any radionuclide other than the first calibration radionuclide and/or wherein the second calibration sample does not comprise any radionuclide other than the second calibration radionuclide.

In certain embodiments, the measure of pulse shape is or is a function of a measure of pulse or tail area divided by pulse amplitude.

In certain embodiments, the FOM is computed as efficiency$^2$/spill.

In certain embodiments, the accepted setting of the first discriminator setting and the second discriminator setting is an optimized setting that maximizes the FOM.

In certain embodiments, the method comprises sorting, by the processor, each of the finite detected radioactive events according to its measure of pulse shape into one of at least three categories using distinct first and second discriminator settings, where the event is identified as originating from a first kind of radionuclide if its pulse shape has a value below the accepted first discriminator setting, the event is identified as originating from a second kind of radionuclide if its pulse shape has a value above the accepted second discriminator setting, and the event is identified as indeterminate if its pulse shape has a value between the accepted first and the accepted second discriminator settings.

In certain embodiments, the event is identified as originating from a beta emitter if its pulse shape has a value below the accepted first discriminator setting and the event is identified as originating from an alpha emitter if its pulse shape has a value above the accepted second discriminator setting, where the accepted first discriminator setting is lower than the accepted second discriminator setting. In certain embodiments, the sorted events include a non-zero number of events in each of three categories—events originating from the first kind of radionuclide, events originating from the second kind of radionuclide, and indeterminate events.

In certain embodiments, the measure of the first radionuclide is or is a function of a sum of sorted events having a pulse shape value below the accepted first discriminator setting and where the measure of the second radionuclide is or is a function of a sum of sorted events having a pulse shape value above the accepted second discriminator setting.

In another aspect, the invention is directed to a radiation detection system for quantifying two or more kinds of radionuclides present in a test sample, the system comprising: a detector for producing a pulse signal corresponding to each of a plurality of detected radioactive events in a test sample; a processor; and a memory having instructions stored thereon, wherein the instructions, when executed by the processor, cause the processor to: for each of the plurality of detected radioactive events in the test sample, obtain a measure of pulse shape from the corresponding pulse signal, where the measure is a function of pulse intensity and pulse duration; sort each of the detected radioactive events according to its measure of pulse shape into one of at least three categories using distinct first and second discriminator settings, where the event is identified as originating from a first kind of radionuclide if its pulse shape has a value below the first discriminator setting, the event is identified as originating from a second kind of radionuclide if its pulse shape has a value above the second discriminator setting, and the event is identified as indeterminate if its pulse shape has a value between the first and second discriminator settings; and display a measure of the first kind of radionuclide and a measure of the second kind of radionuclide.

In certain embodiments, the two or more kinds of radionuclides comprise a beta emitter and an alpha emitter.

In certain embodiments, the detector is a liquid scintillation counter comprising one or more photomultiplier tubes.

In certain embodiments, the test sample is a cocktail comprising a sample material, a solvent for the sample material, and a scintillator, and the sample material comprises a radionuclide that undergoes radioactive decay, whereby the decay energy causes excitation of the scintillator and release of UV light that is detected. In certain embodiments, the scintillator is a fluor.

In certain embodiments, the corresponding pulse signal is a measure of detected light intensity as a function of time.

In certain embodiments, the measure of pulse shape is or is a function of a measure of pulse or tail area divided by pulse amplitude.

In certain embodiments, the event is identified as originating from a beta emitter if its pulse shape has a value below the first discriminator setting and the event is identified as originating from an alpha emitter if its pulse shape has a value above the second discriminator setting, where the first discriminator setting is lower than the second discriminator setting. In certain embodiments, the sorted events include a non-zero number of events in each of three categories—events originating from the first kind of radionuclide, events originating from the second kind of radionuclide, and indeterminate events.

In certain embodiments, the measure of the first kind of radionuclide is or is a function of a sum of sorted events having a pulse shape value below the first discriminator setting, and the measure of the second kind of radionuclide is or is a function of a sum of sorted events having a pulse shape value above the second discriminator setting.

In another aspect, the invention is directed to a radiation detection system featuring automatic calibration for quantification of two or more kinds of radionuclides present in a test sample, the system comprising: a detector for producing a pulse signal corresponding to each of a plurality of detected radioactive events in a test sample; a processor; and a memory having instructions stored thereon, wherein the instructions, when executed by the processor, cause the processor to: receive data corresponding to a measure of pulse shape for each of a plurality of finite detected radioactive events in a first calibration sample comprising a first calibration radionuclide that is the same kind of emitter as and is or is similar to a first radionuclide in the test sample; receive data corresponding to a measure of pulse shape for each of a plurality of finite detected radioactive events in a second calibration sample comprising a second calibration radionuclide that is the same kind of emitter as and is or is similar to a second radionuclide in the test sample; for each of a plurality of settings of both of a first discriminator setting and a second discriminator setting (different from the first discriminator setting), automatically determine, for each of the first and second calibration radionuclides: (i) a measure of spill and (ii) a measure of efficiency, where an event is identified as originating from the first calibration radionuclide if its pulse shape value is below the first discriminator setting, the event is identified as originating from the second calibration radionuclide if its pulse shape value is above the second discriminator setting, and the event is identified as indeterminate if its pulse shape value is between the first and second discriminator settings; compute a figure of merit (FOM) corresponding to each of the plurality of settings of the first discriminator setting and the second discriminator setting, where the FOM is a function of spill and efficiency; determine an accepted setting of the first discriminator setting and the second discriminator setting that produces an acceptably high FOM; obtain, for each of a plurality of detected radioactive events in the test sample, a measure of pulse shape; sort each of the detected radioactive events in the test sample according to its measure of pulse shape using the accepted setting of the first discriminator setting and the second discriminator setting; and display a measure of the first radionuclide in the test sample and the second radionuclide in the test sample according to the accepted setting of the first discriminator setting and the second discriminator setting.

In certain embodiments, the first radionuclide in the test sample is a beta emitter and the second radionuclide in the test sample is an alpha emitter.

In certain embodiments, the detector is a liquid scintillation counter comprising one or more photomultiplier tubes.

In certain embodiments, the test sample is a cocktail comprising a sample material, a solvent for the sample material, and a scintillator, and the sample material comprises a radionuclide that undergoes radioactive decay, whereby the decay energy causes excitation of the scintillator and release of UV light that is detected. In certain embodiments, the scintillator is a fluor.

In certain embodiments, the corresponding pulse signal is a measure of detected light intensity as a function of time.

In certain embodiments, the first calibration sample does not comprise any radionuclide other than the first calibration radionuclide and/or wherein the second calibration sample does not comprise any radionuclide other than the second calibration radionuclide.

In certain embodiments, the measure of pulse shape is or is a function of a measure of pulse or tail area divided by pulse amplitude.

In certain embodiments, the FOM is computed as efficiency$^2$/spill.

In certain embodiments, the accepted setting of the first discriminator setting and the second discriminator setting is an optimized setting that maximizes the FOM.

In certain embodiments, the instructions, when executed by the processor, cause the processor to sort each of the finite detected radioactive events according to its measure of pulse shape into one of at least three categories using distinct first and second discriminator settings, where the event is identified as originating from a first kind of radionuclide if its pulse shape has a value below the accepted first discriminator setting, the event is identified as originating from a second kind of radionuclide if its pulse shape has a value above the accepted second discriminator setting, and the event is identified as indeterminate if its pulse shape has a value between the accepted first and the accepted second discriminator settings.

In certain embodiments, the event is identified as originating from a beta emitter if its pulse shape has a value below the accepted first discriminator setting and the event is identified as originating from an alpha emitter if its pulse shape has a value above the accepted second discriminator setting, where the accepted first discriminator setting is lower than the accepted second discriminator setting. In certain embodiments, the sorted events include a non-zero number of events in each of three categories—events originating from the first kind of radionuclide, events originating from the second kind of radionuclide, and indeterminate events.

In certain embodiments, the measure of the first radionuclide is or is a function of a sum of sorted events having a pulse shape value below the accepted first discriminator setting and where the measure of the second radionuclide is or is a function of a sum of sorted events having a pulse shape value above the accepted second discriminator setting.

In another aspect, the invention is directed to a radiation detection system for applying discriminator settings in the quantification of radionuclides present in a test sample, the system comprising: a detector for producing a pulse signal corresponding to each of a plurality of detected radioactive events in a test sample; a processor; and a memory having instructions stored thereon, wherein the instructions, when executed by the processor, cause the processor to: receive data corresponding to a measure of pulse shape for each of a plurality of finite detected radioactive events in a first calibration sample comprising a first calibration radionuclide that is the same kind of emitter as and is or is similar to a first radionuclide in the test sample; receive data corresponding to a measure of pulse shape for each of a plurality of finite detected radioactive events in a second calibration sample comprising a second calibration radionuclide that is the same kind of emitter as and is or is similar to a second radionuclide in the test sample; display a graphical representation of differentiated radioactive events corresponding to the first and second calibration samples as a function of corresponding measure of pulse shape; display a graphical user interface element allowing adjustment of one or both of a first discriminator setting, and a second discriminator setting, and where an event is identified as originating from the first radionuclide if its pulse shape value is below the first discriminator setting, the event is identified as originating from the second radionuclide if its pulse shape value is above the second discriminator setting, and the event is identified as indeterminate if its pulse shape value is between the first and second discriminator settings; receive a selection by a user of a setting of the graphical user interface element defining the first and second discriminator settings; determine and display a measure of spill and/or a measure of efficiency for each of the first and second calibration radionuclides given the user-selected setting of the graphical user interface element; receive an adjusted setting of the graphical user interface element corresponding to one or both of an adjusted first discriminator setting, and an adjusted second discriminator setting; obtain, for each of a plurality of finite detected radioactive events in the test sample, a measure of pulse shape; sort each of the finite detected radioactive events in the test sample according to its measure of pulse shape using the adjusted setting of the graphical user interface element; and display a measure of the first radionuclide in the test sample and the second radionuclide in the test sample according to the adjusted setting of the graphical user interface element.

In certain embodiments, the first radionuclide in the test sample is a beta emitter and the second radionuclide in the test sample is an alpha emitter.

In certain embodiments, the detector is a liquid scintillation counter comprising one or more photomultiplier tubes.

In certain embodiments, the test sample is a cocktail comprising a sample material, a solvent for the sample material, and a scintillator, and the sample material comprises a radionuclide that undergoes radioactive decay, whereby the decay energy causes excitation of the scintillator and release of UV light that is detected. In certain embodiments, the scintillator is a fluor.

In certain embodiments, the corresponding pulse signal is a measure of detected light intensity as a function of time.

In certain embodiments, the first calibration sample does not comprise any radionuclide other than the first calibration radionuclide and/or wherein the second calibration sample does not comprise any radionuclide other than the second calibration radionuclide.

In certain embodiments, the measure of pulse shape is or is a function of a measure of pulse or tail area divided by pulse amplitude.

In certain embodiments, the graphical representation of differentiated radioactive events comprises a histogram and/or a computation of % spill.

In certain embodiments, the adjusted setting is a user-adjusted setting.

In certain embodiments, the instructions cause the processor to sort each of the finite detected radioactive events in the test sample according to its measure of pulse shape using the adjusted first discriminator setting and the adjusted second discriminator setting.

In certain embodiments, the instruction cause the processor to sort each of the finite detected radioactive events according to its measure of pulse shape into one of at least three categories using distinct first and second discriminator settings, where the event is identified as originating from a first kind of radionuclide if its pulse shape has a value below the adjusted first discriminator setting, the event is identified as originating from a second kind of radionuclide if its pulse shape has a value above the adjusted second discriminator setting, and the event is identified as indeterminate if its pulse shape has a value between the adjusted first and the adjusted second discriminator settings. In certain embodiments, the event is identified as originating from a beta emitter if its pulse shape has a value below the adjusted first discriminator setting and the event is identified as originating from an alpha emitter if its pulse shape has a value above the adjusted second discriminator setting, where the adjusted first discriminator setting is lower than the adjusted second discriminator setting. In certain embodiments, the sorted events include a non-zero number of events in each of three categories—events originating from the first kind of radionuclide, events originating from the second kind of radionuclide, and indeterminate events.

In certain embodiments, the measure of the first kind of radionuclide in the test sample is or is a function of a sum of sorted events having a pulse shape value below the adjusted first discriminator setting, and the measure of the second kind of radionuclide in the test sample is or is a function of a sum of sorted events having a pulse shape value above the adjusted second discriminator setting.

Embodiments described with respect to one aspect of the invention may be, applied to another aspect of the invention (e.g., features of embodiments described with respect to one independent claim, e.g., a method claim, are contemplated to be applicable to other embodiments of other independent claims, e.g., a system claim, and vice versa).

DESCRIPTION OF THE DRAWINGS

The foregoing and other objects, aspects, features, and advantages of the invention will become more apparent and may be better understood by referring to the following description taken in conjunction with the accompanying drawings, in which.

DETAILED DESCRIPTION

It is contemplated that systems, devices, methods, and processes of the claimed invention encompass variations and adaptations developed using information from the embodiments described herein. Adaptation and/or modification of the systems, devices, methods, and processes described herein may be performed by those of ordinary skill in the relevant art.

Throughout the description, where articles, devices, and systems are described as having, including, or comprising specific components, or where processes and methods are described as having, including, or comprising specific steps, it is contemplated that, additionally, there are articles, devices, and systems of the present invention that consist essentially of, or consist of, the recited components, and that there are processes and methods according to the present invention that consist essentially of, or consist of, the recited processing steps.

It should be understood that the order of steps or order for performing certain action is immaterial so long as the invention remains operable. Moreover, two or more steps or actions may be conducted simultaneously.

The mention herein of any publication, for example, in the Background section, is not an admission that the publication serves as prior art with respect to any of the claims presented herein. The Background section is presented for purposes of clarity and is not meant as a description of prior art with respect to any claim.

Liquid scintillation counter systems, such as the Quantulus™ GCT LSC and Tri-Carb® LSC product lines, manufactured by PerkinElmer headquartered in Waltham, Mass., are useful for highly precise quantification of radionuclides in test samples. Presented herein are systems and methods that address discrimination between radioactive events, in particular, the reduction of alpha/beta misclassification (spill) in LSC systems for improved discrimination.

Figure 1A:
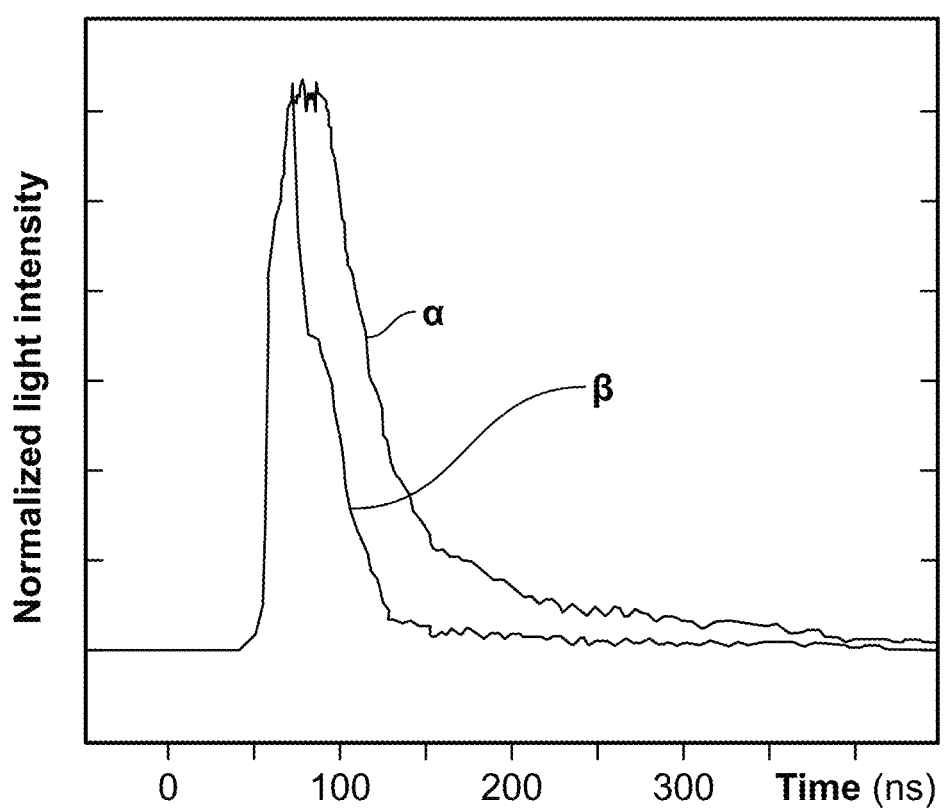
FIG. 1A is a plot showing normalized light intensity as measured by a liquid scintillation counter (LSC) as a function of time, demonstrating different pulse shapes associated with an alpha emitter vs. a beta emitter.

Use of a single alpha/beta discriminator value, while helpful, can produce relatively high levels of misclassification of events for certain applications. For example, a pulse shape analysis (PSA) value is computed for a particular event and compared against a single discriminator value to determine whether the event represents an alpha event or a beta event. In certain embodiments, the PSA value for a given event is computed as normalized peak energy of the event divided by the sum of the energy curve for at least part of the event (e.g., the tail of the event, defined as a portion following peak, or another portion (or all) of the curve). The PSA value can be measured in a number of ways, so long as the value allows discrimination between alpha events and beta events, where alpha events are known to have comparatively longer tails, as depicted in FIG. 1A. For example, in some embodiments, the PSA value is a measure of pulse amplitude (total signal) divided by pulse length. In some embodiments, the PSA value is a measure of pulse amplitude divided by a normalized pulse length (pulse length normalized to pulse amplitude). For any of the quantities given here, its inverse can also be used as a discriminator. Where there is a single discriminator, the PSA for a given event is compared against the discriminator to determine whether the event is alpha or beta.

Figure 1B:
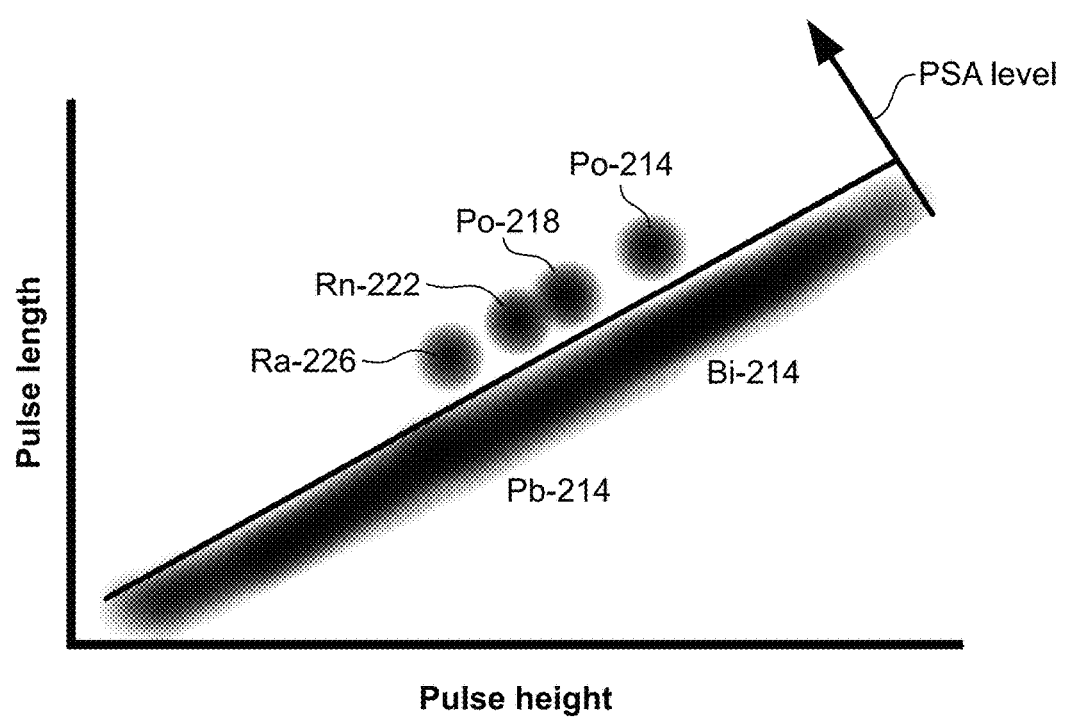
FIG. 1B is a plot showing division of pulses into alpha and beta spectra by dividing the pulse amplitude/length plane in two parts by a straight line; pulses above the line are directed into the long pulse spectrum (alpha spectrum), pulses below the line are directed into the short pulse spectrum (beta spectrum).
Figure 1C:
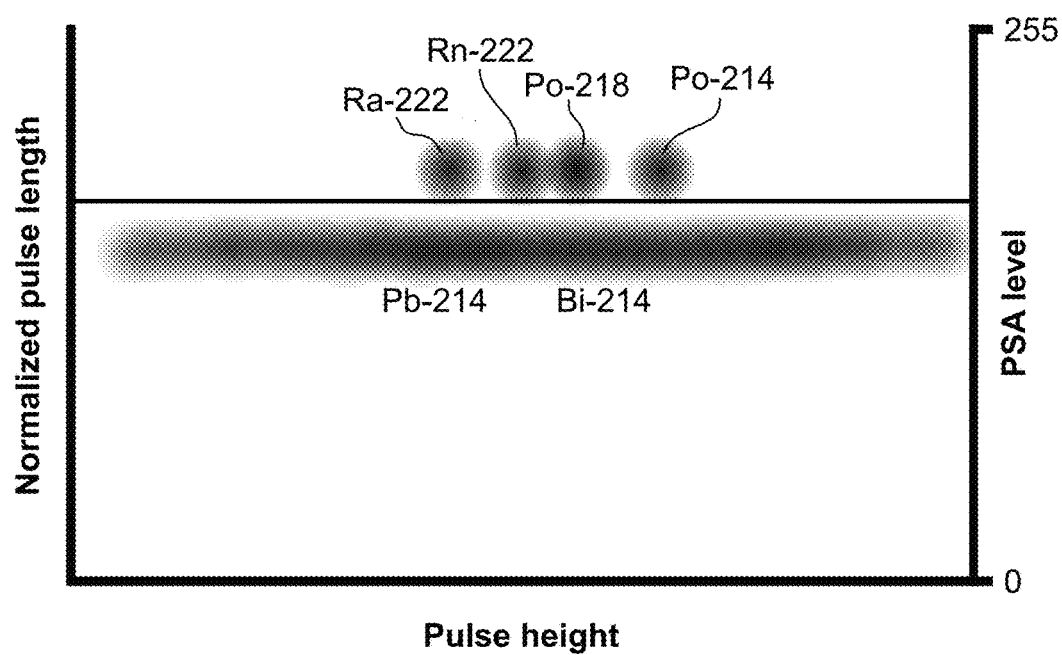
FIG. 1C is a plot of the data shown in 1B with a normalized pulse length as the vertical axis, demonstrating determination of a threshold PSA value (single discriminator) separating alpha emissions from beta emissions.

FIG. 1B is a plot of pulse height vs. pulse length, where alpha/beta pulse amplitude (energy) is transformed to a three dimensional counts vs. pulse amplitude and pulse spectrum. Pulses can be separated into alpha and beta spectra by dividing the pulse amplitude/length plane into two parts with a straight line. Pulses above the line are directed into the long pulse spectrum and are identified as alpha (e.g., Ra-226, Ra-222, Po-218, and Po-214 shown in FIG. 1B), while pulses below the line are directed into the short pulse spectrum and are identified as beta (e.g., Pb-214 and Bi-214 shown in FIG. 1B). Settings can be chosen to conform with various solvents, fluors, and quench levels. FIG. 1C is a plot of the data in FIG. 1B, but with a normalized pulse length as the vertical axis. The single PSA discriminator value is shown as the horizontal line dividing the alpha emitters from the beta emitters.

Some isotopes, such as beta isotope Strontium-90 ($^{90}$Sr), are more difficult to distinguish than others, due to their pulse shapes. As an illustration, using the Tri-Carb® GLO product line with a single discriminator setting, misclassification error (spill) is 1.54%/1.58% (spill into alpha/spill into beta) with beta emitter $^{90}$Sr and alpha emitter Americium-241 ($^{241}$Am), while the misclassification error using the same instrument is significantly lower—0.22%/0.23%— for beta emitter Chlorine-36 ($^{36}$Cl) and alpha emitter $^{241}$Am.

It is surprisingly found that use of multiple (e.g., first and second) discriminator settings separated by a non-zero value (e.g., a gap or trench) results in significantly reduced misclassification error while permitting user flexibility in minimizing the resulting loss of efficiency (% events lost due to classification as "indeterminate"). For example, the larger the gap, the greater the loss of efficiency, but for some applications, the tradeoff is worth it, so having the adjustment option available is important. In certain embodiments, a graphical user interface as described herein provides a more intuitive, more flexible user experience in determining the multiple discriminator settings via presentation of a histogram with adjustable discriminator values so that the spill/efficiency tradeoff can be set in much less time, and with more favorable results. This reduces the previous time required for alpha/beta discriminator setup from over an hour to just a few minutes, in addition to providing the increased flexibility and spill reduction of multiple discriminator settings.

Table 1 below compares the detected events classified as beta events and alpha events for $^{90}$Sr (pure beta emitter) and $^{241}$Am (pure alpha emitter). The first example shows use of PSA of 141 for both the lower and upper discriminator settings. There is considerable mischaracterization of alpha and beta events (1.54% beta events mischaracterized as alpha, and 1.58% alpha events mischaracterized as beta). By choosing two discriminator settings such that events with PSA value between the discriminators are considered indeterminate, the spill is reduced. Accordingly, the second example shows use of 128 as lower discriminator setting and 160 as an upper discriminator setting, which results in a % spill into alpha of 0.39% and a % spill into beta of 0.52%, a significant reduction as compared to use of a single discriminator setting. Note that the % events lost due to their PSA values falling between the two discriminator settings is 6.86% for $^{90}$Sr and 3.05% for $^{241}$Am. This loss of efficiency may be acceptable for a given application, depending on the needs of the user. The third example shown in Table 1 shows an even larger gap between the upper and lower discriminator settings, resulting in a further reduced spill, though with a further loss of efficiency.

Thus, with incorporation of upper and lower PSA value discriminator settings, $^{241}$Am and $^{90}$Sr alpha/beta separation spill was reduced from about 1.5% (no gap) to a 0.5% spill with a gap of 32 PSA values wide. Efficiency loss was less than 7%. Where higher efficiency loss can be tolerated (e.g., about 19%), spills of less than 0.3% can be achieved using a wider gap, e.g., 64 PSA values.

TABLE 1 demonstration of reduced alpha/beta spill using multiple PSA discriminator settings

| Moat = 0/ Disc = 141 | Beta events (0 to 2000 KeV) | Alpha Event (0 to 1000 KeV) | % spill into Alpha | % spill into Beta | Total Counts |
|---|---|---|---|---|---|
| 90SR CPM | 18938 | 297 | 1.54% | | 19235 |
| 241AM CPM | 781 | 48767 | | 1.58% | 48548 |

| Moat = 32/ Disc = 128 | Beta events (0 to 2000 KeV) | Alpha Event (0 to 1000 KeV) | % spill into Alpha | % spill into Beta | % events lost due to moat |
|---|---|---|---|---|---|
| 90SR CPM | 17846 | 70 | 0.39% | | 6.86% |
| 241AM CPM | 246 | 46822 | | 0.52% | 3.05% |

| Moat = 64/ Disc = 103 | Beta events (0 to 2000 KeV) | Alpha Event (0 to 1000 KeV) | % spill into Alpha | % spill into Beta | % events lost due to moat |
|---|---|---|---|---|---|
| 90SR CPM | 15651 | 17 | 0.11% | | 18.54% |
| 241AM CPM | 115 | 44749 | | 0.26% | 7.59% |

Figure 2A:
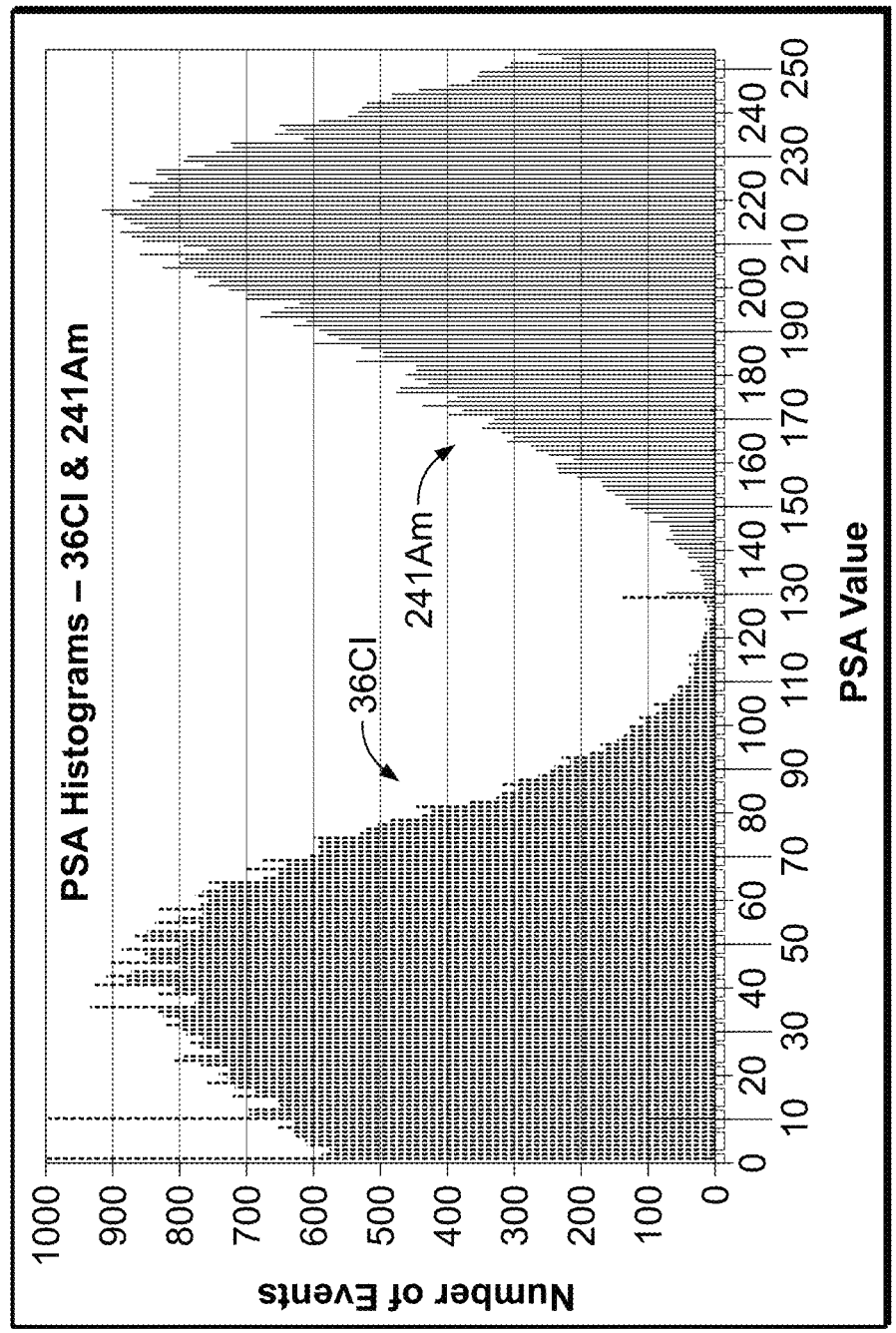
FIG. 2A shows a graphical user interface histogram element for adjustment of one or more discriminator settings for quantification of radionuclides in a test sample, according to an illustrative embodiment of the invention.

FIG. 2A depicts a graphical user interface element featuring a histogram plot that allows for adjustment of multiple discriminator settings for quantification of radionuclides in a test sample. Use of the histogram user interface element reduces the time needed for a user to find optimal discrimination values for a particular application from over an hour to just a few minutes. In certain embodiments, the histogram is a plot of PSA value (x-axis) vs. number of counts (y-axis) and efficiency ($2^{nd}$ y-axis) for an alpha/beta standards assay, which can be used to quickly optimize the discriminator settings and amount of gap to use. As used herein, a graphical user interface element can be a window, slider, toggle, check box, drop box, radio button, a line, a set of lines, a shaded area, or any other graphical object, or any combination of the above, with which a user can interact via a display to adjust one or more settings.

FIG. 2A depicts a histogram showing the number of events (counts) having a given computed PSA value (or PSA value range or bin). The number of events detected from a calibration sample containing $^{36}$Cl (known beta) having a given PSA value are depicted in blue (corresponding to the left peak), the number of events detected from a calibration sample containing $^{241}$Am (known alpha) having a given PSA value are depicted in red (corresponding to the right peak). Note that there is some overlap between the two peaks in the range of PSA values from about 120 to about 130.

Figure 2B:
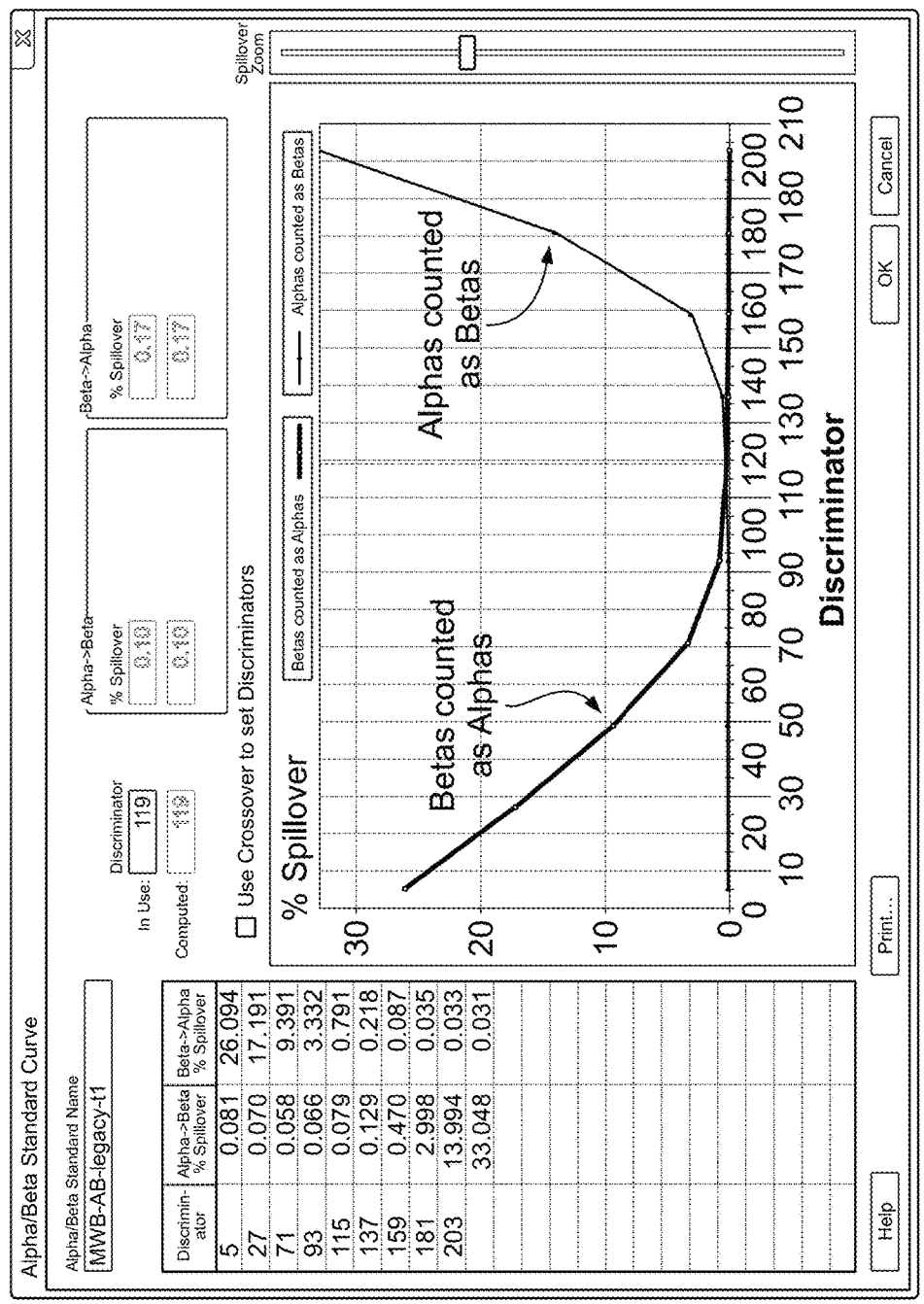
FIG. 2B shows a graphical user interface element (window) depicting % spillover (% alphas counted as betas and % betas counted as alphas) as a function of a (single) PSA discriminator setting, according to an illustrative embodiment of the invention.

FIG. 2B shows a graphical user interface element depicting % spill as a function of a (single) PSA discriminator setting. The GUI can be a text box in which a discriminator value can be entered, a vertical line that can be adjusted on the plot, or a slider bar, for example. This GUI allows a user to adjust the PSA discriminator setting, thereby adjusting the two different % spillover quantities. That is, at any given PSA discriminator setting, there will be a % alphas mistakenly counted as betas and a % betas mistakenly counted as alphas using the given setting. For a given application, it may be more important to minimize one kind of spill versus another, depending on which species is of most interest in a test sample to be run following the PSA discriminator setting calibration.

Figure 2C:
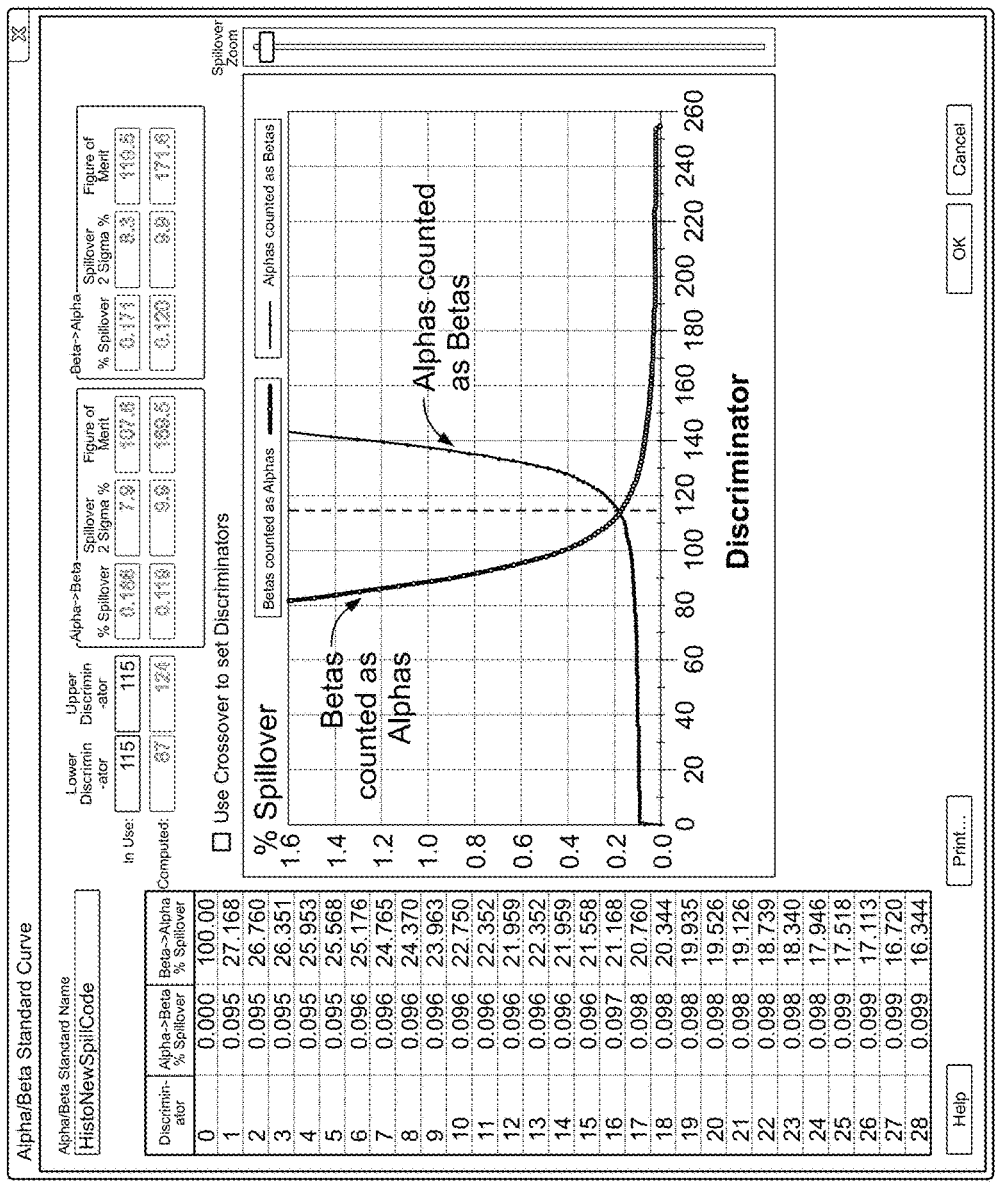
FIG. 2C shows a graphical user interface element (window) depicting % spillover (% alphas counted as betas and % betas counted as alphas) as a function of multiple PSA discriminator settings, where the same setting is chosen as lower discriminator and upper discriminator, according to an illustrative embodiment of the invention.

FIG. 2C shows a graphical user interface element depicting % spill as a function of two PSA discriminators—a lower discriminator and an upper discriminator. The values of % spill (both % alphas counted as betas and % betas counted as alphas) are plotted as y-values over a range of discriminator settings (x-values) for a given calibration setup using an alpha standard and a beta standard. A check box can allow a user to automatically select the crossover of the alphas counted as betas and betas counted as alphas curve as a single discriminator, as selected here, where the discriminator is set at a PSA value of 115.

Figure 2D:
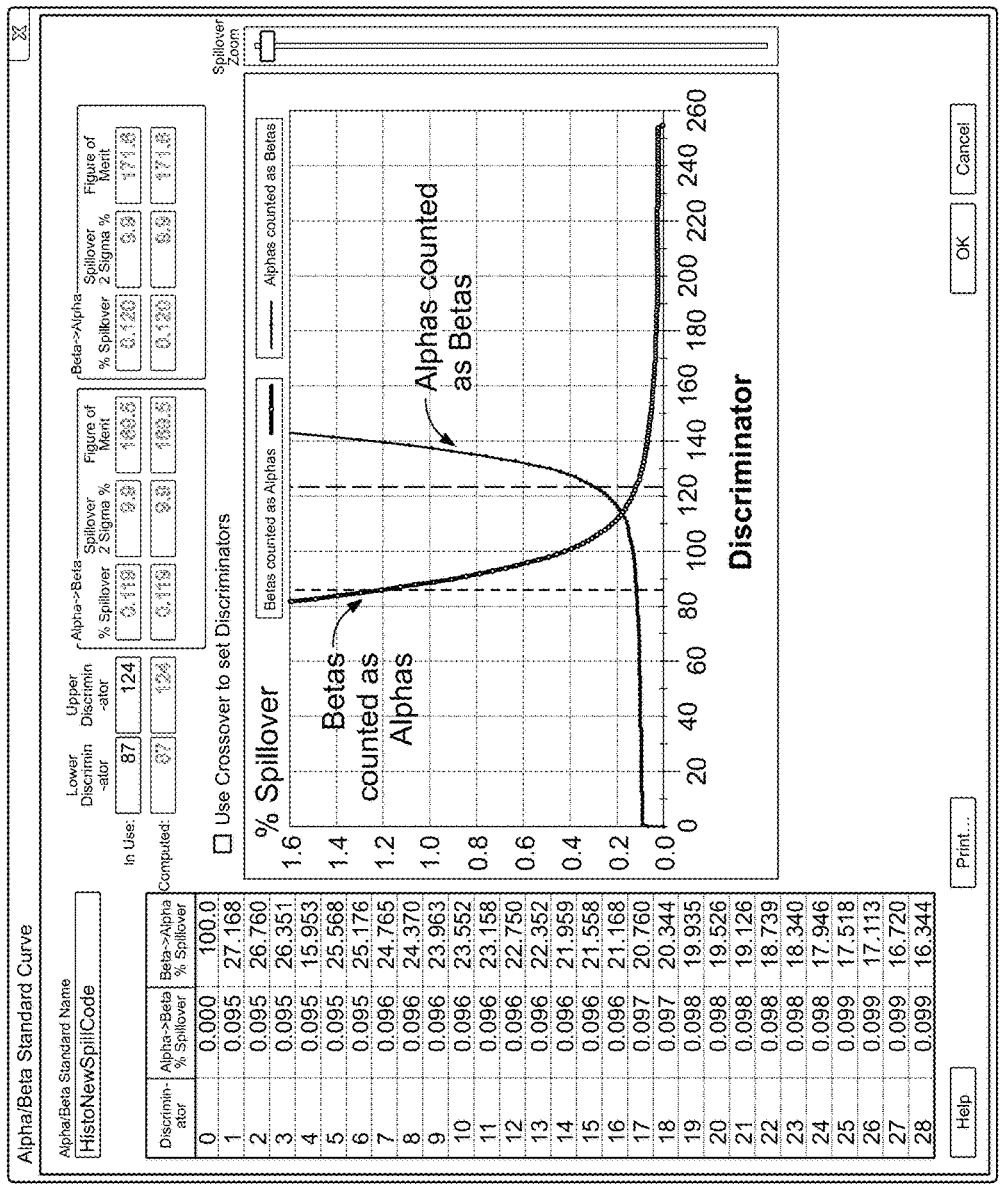
FIG. 2D shows a graphical user interface element (window) depicting % spillover (% alphas counted as betas and % betas counted as alphas) as a function of multiple PSA discriminator settings, where the lower discriminator and upper discriminator are different, according to an illustrative embodiment of the invention.

FIG. 2D shows the graphical user interface element from FIG. 2C, but with two different discriminator values selected—a lower discriminator value and an upper discriminator value. As explained above, events with PSA below the lower discriminator value are considered Type 1 (e.g., beta), events with PSA above the upper discriminator value are considered Type 2 (e.g., alpha), and events with PSA between the upper and lower discriminator values are considered indeterminate. Because there is a non-zero number of indeterminate events, the efficiency will be affected by choice of upper and lower discriminators. The GUI shows Figure of Merit, a function of both efficiency and % spill, which varies depending on the choice of upper and lower discriminators. A user may select to have the system automatically select the lower and upper discriminator that maximizes the Figure of Merit for a given calibration setup. The user may also decide to adjust the upper and lower discriminators by manipulation of the GUI, either by entering discriminator values in the corresponding text boxes, by adjusting a toggle, and/or by adjusting vertical lines on the plot representing the discriminator values.

Figure 3:
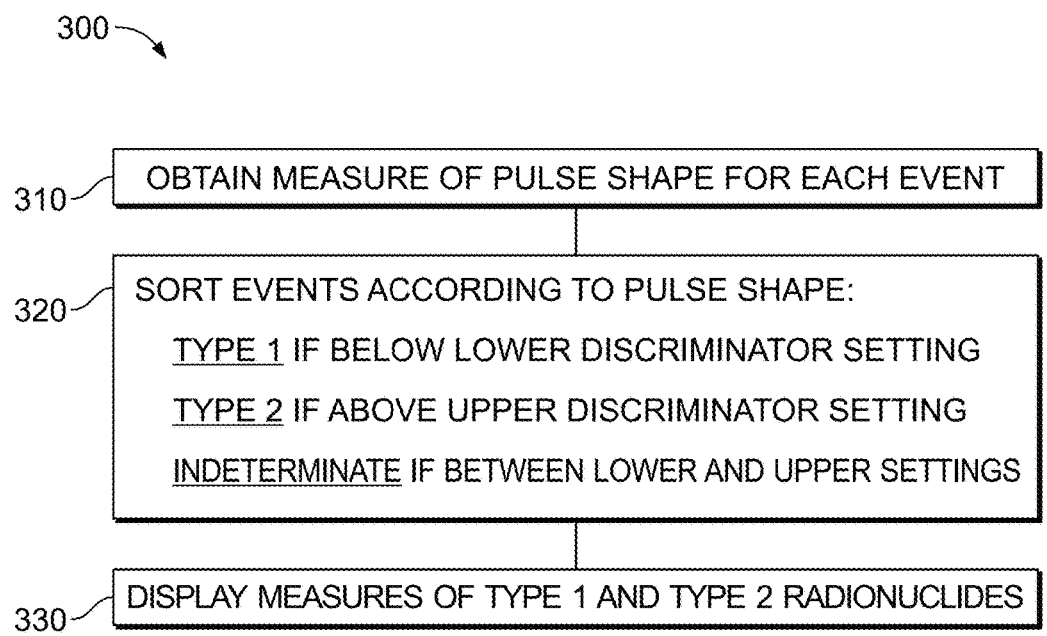
FIG. 3 is a block flow diagram of a method for quantifying two or more kinds of radionuclides present in a test sample using multiple predetermined discriminator settings, according to an illustrative embodiment of the invention.

FIG. 3 is a block flow diagram of a method 300 for quantifying two or more kinds of radionuclides present in a test sample using multiple predetermined discriminator settings, according to an illustrative embodiment. In step 310, a measure of pulse shape is obtained for each detected event. For example, the events may be detected using a scintillator system, e.g., an LSC, and a PSA value for each detected event may be computed as described elsewhere herein. For the given test sample, a calibration study may have been conducted prior to the test sample run using standards containing radionuclides that are the same as or similar to the radionuclides expected to be in the test sample, where both upper and lower PSA discriminator settings have been determined either automatically or set by a user based on the calibration study. In step 320, each detected event from the test sample run is sorted as either Type 1, Type 2, or indeterminate, based on whether its measure of pulse shape (e.g., PSA value) is below the lower discriminator setting, above the upper discriminator setting, or between the lower and upper settings. Then, in step 330, measures of the Type 1 and Type 2 radionuclides are displayed.

In certain embodiments, the measures of Type 1 and Type 2 radionuclides in step 330 of FIG. 3 are simply the sorted counts themselves (e.g., raw numbers of counts, percentages, or other quantification based on detected counts). In other embodiments, the measures are concentrations of radionuclides in the sample. Furthermore, in certain embodiments, there may be more than one species of radionuclide present in the sample that is a Type 1 emitter, and/or there may be more than one kind of radionuclide present in the sample that is a Type 2 emitter. Further identification or quantification of species of a given type in a sample may be made using PSA values, or other values detected by LSC and/or by use of another analytical technique (e.g., liquid or solid scintillation, spectrometry, mass spectrometry (e.g., ICP-MS), HPGe and/or NaI system, XRF system, Geiger-Mueller counter, gas flow proportional counter (GPC), and/or pressurized ionization chamber (PIC)). These techniques can be used alone or in combination. That is, in addition to the radiation type discrimination techniques described herein (e.g., for alpha v. beta, alpha v. gamma, beta v. gamma, or alpha v. beta v. gamma discrimination), the determination of the identity and/or quantity of radionuclides in a sample within a given category (e.g., alpha, beta, or gamma emitter) may also include analysis of the sample by one or more additional analytical techniques (e.g., for example, used in combination with LSC). Furthermore, the discrimination techniques described herein using LSC may account for choice of solvent, fluor, and quench by known methods.

In certain embodiments, the LSC process may implement guard compensation technology as described in U.S. Pat. No. 9,297,909, "Guard Efficiency Compensation System and Method," issued Mar. 29, 2016. The LSC system may feature replay assay reprocessing, allowing change of measurement parameters without rerunning the assay. The LSC system may also provide for high sample throughput (e.g., running more than 100, more than 200, or more than 400 vials at once).

Figure 4:
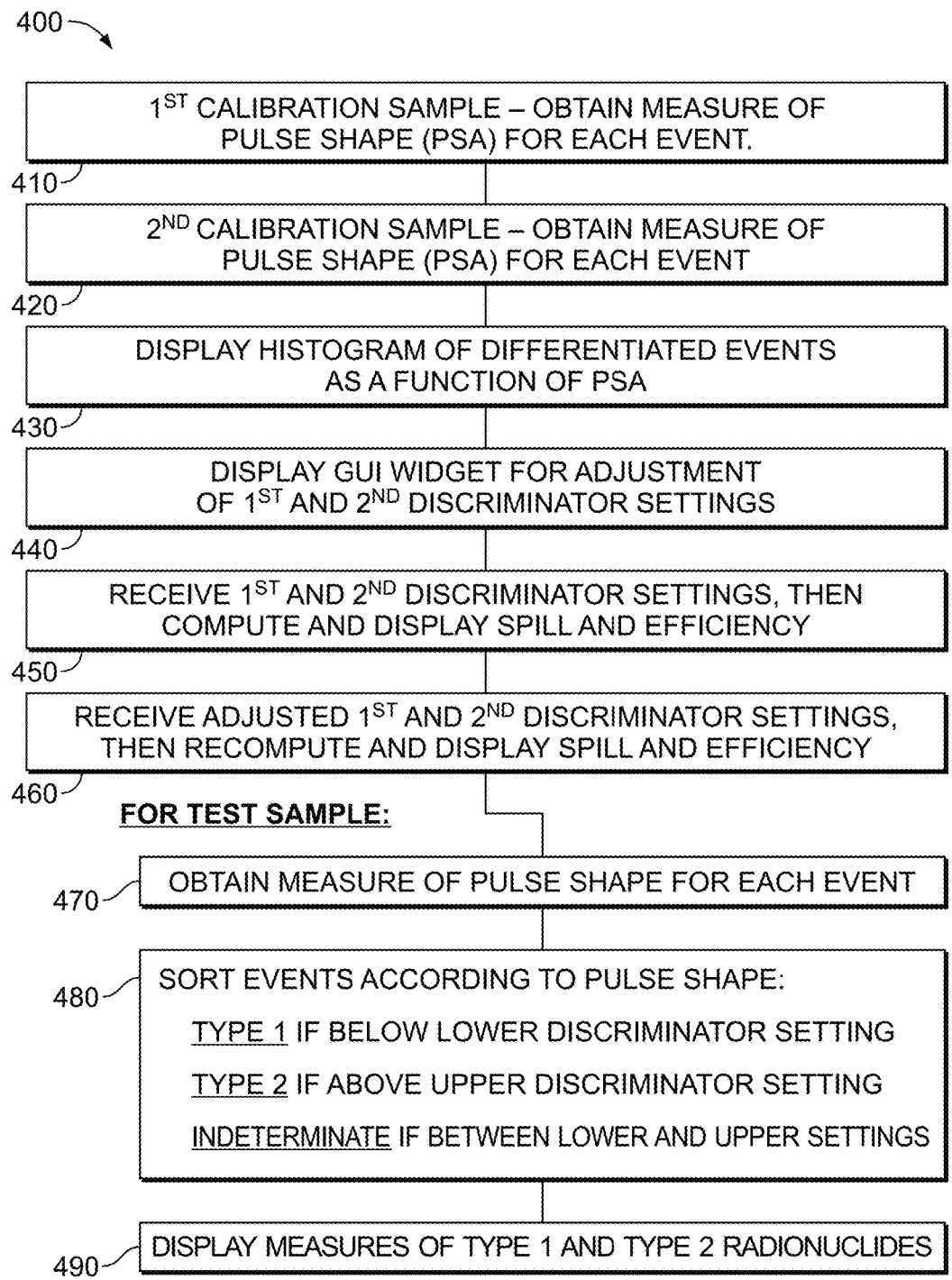
FIG. 4 is a block flow diagram of a method for allowing adjustment of multiple discriminator settings during user calibration via a graphical user interface element, followed by use of the adjusted discriminator settings for quantification of radionuclides in a test sample, according to an illustrative embodiment of the invention.

FIG. 4 is a block flow diagram of a method 400 that allows for adjustment of multiple discriminator settings during user calibration with known standards, followed by use of the adjusted discriminator settings for quantification of radionuclides in a test sample. Calibration standards that are the same as or similar to the radionuclides expected to be in the test sample can be used, for example. In step 410, measures of pulse shape (e.g., PSA) are obtained for each event detected in a first calibration sample having a first type of radionuclide (e.g., alpha, beta, or gamma), and in step 420, measures of pulse shape are obtained for each event detected in a second calibration sample having a second type of radionuclide different from the first type (e.g., alpha, beta, or gamma). In step 430, a histogram showing differentiated events as a function of PSA is displayed. Alternatively, or additionally, a plot of % spill is shown as a function of PSA. In step 440, a GUI element is displayed for adjustment of first and second (e.g., upper and lower) discriminator settings. In certain embodiments, the settings have different values. In step 450, first and second discriminator settings are received (either automatically received as part of a routine to compute % spill, efficiency, or other values, or received as a selection made by a user), then % spill and efficiency values are computed and displayed for those first and second discriminator settings. In step 460, adjusted first and second discriminator settings are received (either adjusted automatically as part of a routine, or adjusted by user selection), then % spill and efficiency values are computed and displayed for those adjusted first and second (upper and lower) discriminator settings. Step 460 can be repeated for a variety of sets of first and second discriminator settings until a desired final setting is achieved, either automatically (e.g., via maximization of a Figure of Merit value) or as decided by a user.

Now that final first and second (e.g., upper and lower) discriminator settings have been set from the calibration run using the LSC (or other radioactive event detector system), the test sample may be run in the LSC (or other detector system). Thus, in step 470, a measure of pulse shape is obtained for each detected event in the test sample. Then, as explained with respect to steps 320 and 330 of FIG. 3, each event is sorted as a Type 1 event, Type 2 event, or indeterminate event, according to its measure of pulse shape (step 480) using the discriminator settings (e.g., upper and lower settings) determined from the calibration run, and measures of the Type 1 and Type 2 radionuclides in the test sample are computed and displayed (step 490).

Figure 5:
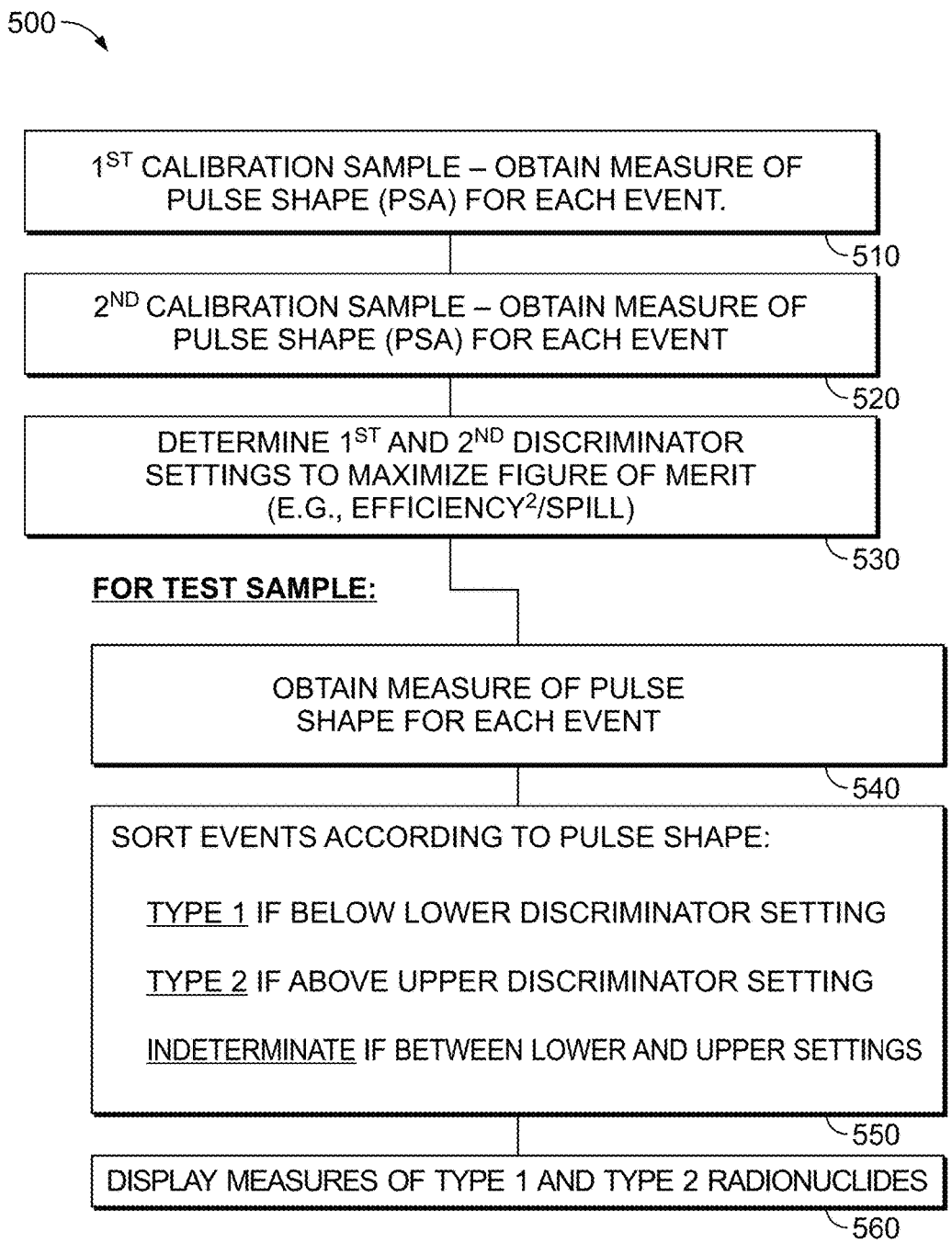
FIG. 5 is a block flow diagram of a method for automated determination of multiple discriminator settings for quantifying two or more kinds of radionuclides present in a test sample, according to an illustrative embodiment of the invention.

FIG. 5 is a block flow diagram of a method similar to that in FIG. 4—that is, the method provides for determination of multiple discriminator settings during calibration then measurement of radionuclides in a test sample using those settings—however, in FIG. 5, the multiple discriminator settings are automatically selected. Thus, during calibration, step 510 is obtaining a measure of pulse shape (e.g., PSA) for each event in a first calibration sample and step 520 is obtaining a measure of pulse shape (e.g., PSA) for each event in a second calibration sample, then step 530 is automated determination of first and second (e.g., upper and lower) pulse shape value discriminator settings to maximize a figure of merit. The figure of merit can be a function of efficiency and % spill, for example, as shown in more detail in the paragraph below. Then, for the test sample, a measure of pulse shape is obtained for each event detected in the test sample (step 540), each event is sorted as Type 1, Type 2, or indeterminate according to its measure of pulse shape using the first and second discriminator settings (e.g., upper and lower discriminator settings) (step 550), then measures of the Type 1 and Type 2 radionuclides are obtained and displayed (step 560).

Presented below for illustrative purposes is an example of code for the automated determination of $1^{st}$ and $2^{nd}$ discriminator settings in step 530 of the method of FIG. 5 is presented as C language code below:

```
// read in .CSV with PSA histogram
ReadABHistogram( );
```

The "ReadABHistogram( );" function obtains the PSA histogram data generated by counting the pure alpha and pure beta calibration samples.

// calc eff and spill for each PSA value
CalcEFFandSpill( );

Efficiency is the detected number of events divided by the actual number of events. Spill is the number of alpha or beta events that have been misclassified. Both efficiency and spill can differ for each PSA discrimination value.

// calc FOMs for each psa hi/lo pair (5 to 250 PSA to remove cases where eff is likely too low)
CalcFOMs( );

In this example, Figure of Merit (FOM) is computed as Efficiency$^2$/spill, similar to S/N, and is determined for alpha events and beta events at each PSA discrimination setting.

// find and output the highest min E$^2$/spill and its associated PSA values
FindHighMinFOM( );

Once the FOMs are calculated, FOMs for pairs of high and low PSA discrimination values are compared. The PSA discriminator values for the pair with the highest minimum of the two is presented as an optimum. For example, if one pair has FOMs of 200 (alpha) and 30 (beta), and another pair has FOMs of 100 (alpha) and 40 (beta), the 100-40 pair would have the highest minimum FOM.

In addition to the specific methods presented here, there are other methods of determining the two discriminator settings (and the difference between the two settings) within the scope of the claimed subject matter.

Moreover, while embodiments are described above with respect to differentiating between two event types, it would be understood the techniques described herein can be applied for differentiating between three or more event types, such techniques being understood to be within the scope of the claimed subject matter.

Figure 6:
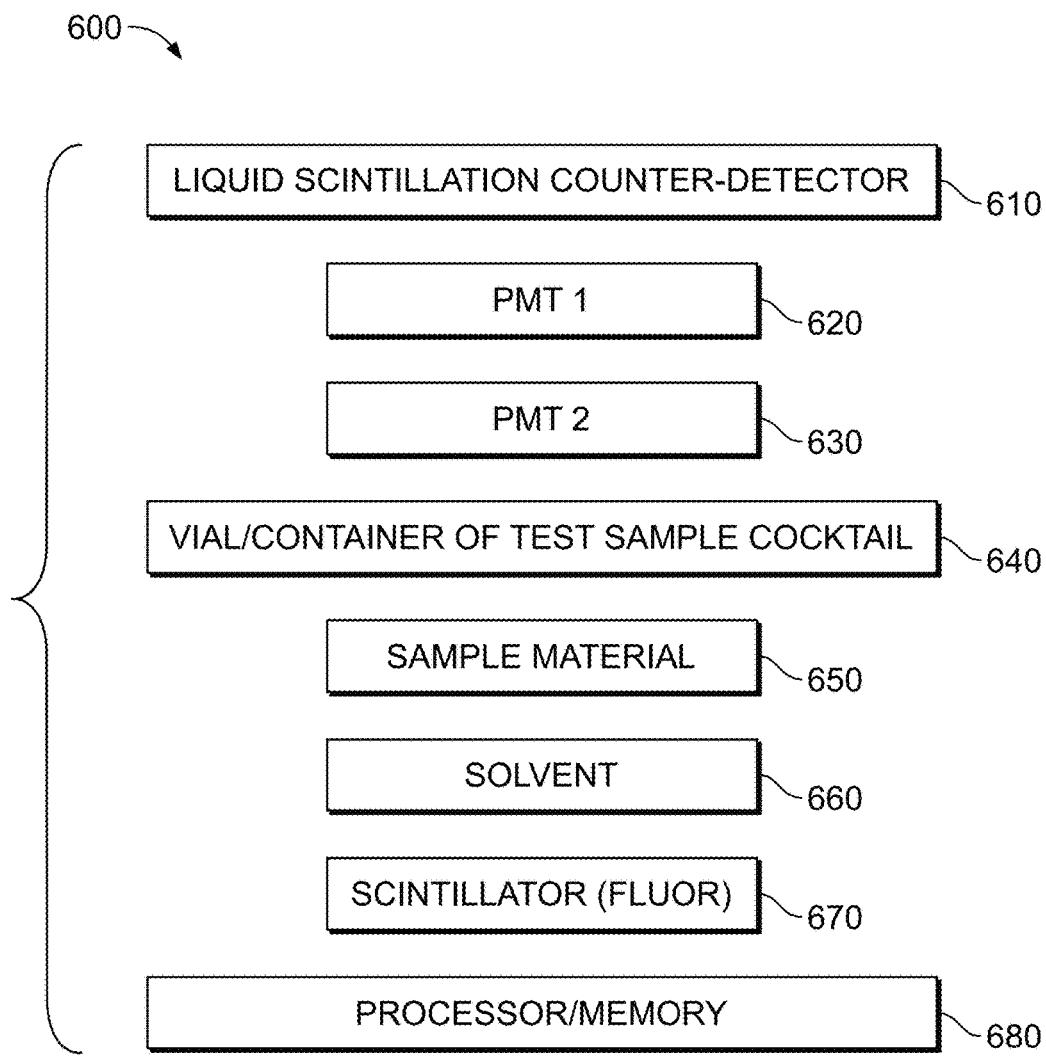
FIG. 6 is a block diagram of a liquid scintillation counting system for quantification of two or more kinds of radionuclides present in a test sample, according to an illustrative embodiment.

FIG. 6 is a block diagram of a liquid scintillation counting (LSC) system 600 for quantification of two or more kinds of radionuclides present in a test sample using the techniques described herein. For example, sample material (650) containing one or more radionuclides to be identified is mixed with a solvent (660) capable of dissolving the sample, along with a scintillator (e.g., a fluor) (670). A vial (or other container) of the resulting test sample cocktail (640) is placed in an LSC detector (610) comprising one or more photomultiplier tubes (PMTs). In FIG. 6, two PMTs are shown, 620 and 630. When the radionuclide(s) undergo radioactive decay, the emitted decay energy causes excitation of the scintillator and release of UV light, which is detected. The intensity of the light is a function of the decay energy, and the shape of the detected pulse can be used to distinguish between different kinds of radioactive events, e.g., alpha, beta, or gamma radiation. The detector produces a pulse signal corresponding to each of a plurality of radioactive events detected in the test sample. The identity and/or quantity of the radionuclide can then be determined. The system also includes a processor and memory having instructions stored thereon, wherein the instructions, when executed by the processor, cause the processor to perform the event type discrimination methods described herein.

Figure 7:
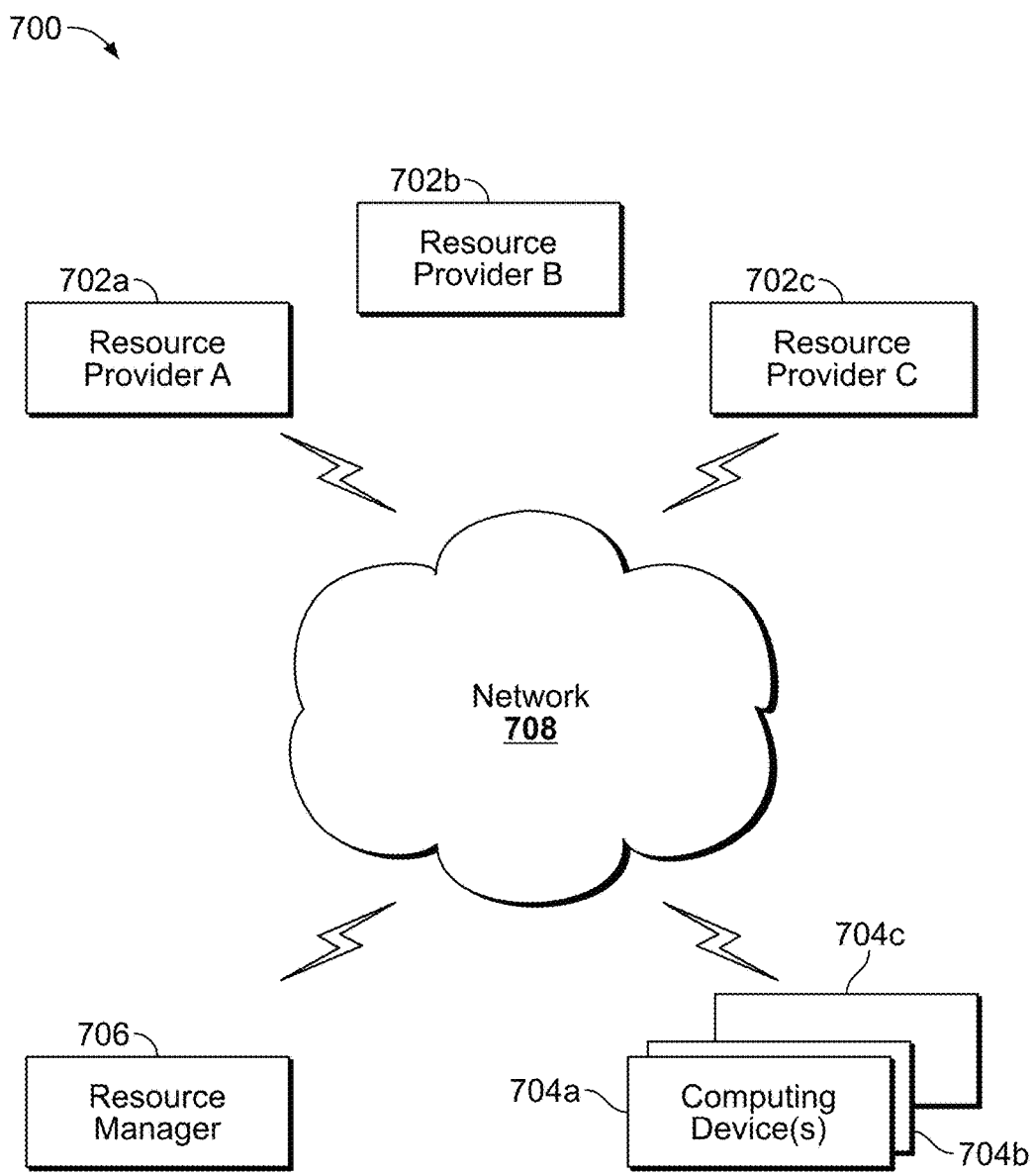
FIG. 7 is a block diagram of an example computing device and an example mobile computing device, for use in illustrative embodiments of the present disclosure.

FIG. 7 shows an illustrative network environment 700 for use in the methods and systems described herein. In brief overview, referring now to FIG. 7, a block diagram of an exemplary cloud computing environment 700 is shown and described. The cloud computing environment 700 may include one or more resource providers 702a, 702b, 702c (collectively, 702). Each resource provider 702 may include computing resources. In some implementations, computing resources may include any hardware and/or software used to process data. For example, computing resources may include hardware and/or software capable of executing algorithms, computer programs, and/or computer applications. In some implementations, exemplary computing resources may include application servers and/or databases with storage and retrieval capabilities. Each resource provider 702 may be connected to any other resource provider 702 in the cloud computing environment 700. In some implementations, the resource providers 702 may be connected over a computer network 708. Each resource provider 702 may be connected to one or more computing device 704a, 704b, 704c (collectively, 704), over the computer network 708.

The cloud computing environment 700 may include a resource manager 706. The resource manager 706 may be connected to the resource providers 702 and the computing devices 704 over the computer network 708. In some implementations, the resource manager 706 may facilitate the provision of computing resources by one or more resource providers 702 to one or more computing devices 704. The resource manager 706 may receive a request for a computing resource from a particular computing device 704. The resource manager 706 may identify one or more resource providers 702 capable of providing the computing resource requested by the computing device 704. The resource manager 706 may select a resource provider 702 to provide the computing resource. The resource manager 706 may facilitate a connection between the resource provider 702 and a particular computing device 704. In some implementations, the resource manager 706 may establish a connection between a particular resource provider 702 and a particular computing device 704. In some implementations, the resource manager 706 may redirect a particular computing device 704 to a particular resource provider 702 with the requested computing resource.

Figure 8:
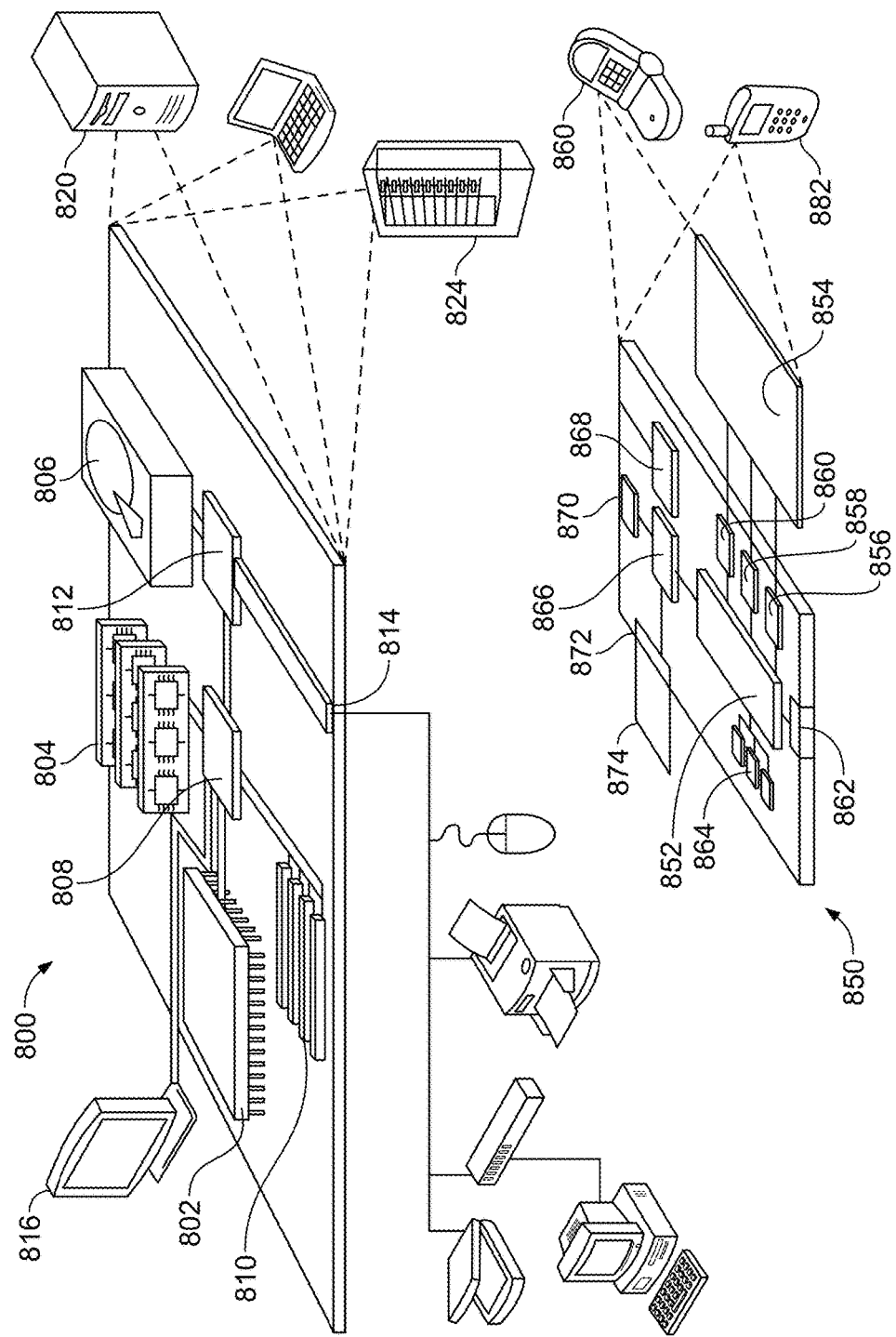
FIG. 8 is a block diagram of an example computing environment, for use in illustrative embodiments of the present disclosure.

FIG. 8 shows an example of a computing device 800 and a mobile computing device 850 that can be used in the methods and systems described in this disclosure. The computing device 800 is intended to represent various forms of digital computers, such as laptops, desktops, workstations, personal digital assistants, servers, blade servers, mainframes, and other appropriate computers. The mobile computing device 850 is intended to represent various forms of mobile devices, such as personal digital assistants, cellular telephones, smart-phones, and other similar computing devices. The components shown here, their connections and relationships, and their functions, are meant to be examples only, and are not meant to be limiting.

The computing device 800 includes a processor 802, a memory 804, a storage device 806, a high-speed interface 808 connecting to the memory 804 and multiple high-speed expansion ports 810, and a low-speed interface 812 connecting to a low-speed expansion port 814 and the storage device 806. Each of the processor 802, the memory 804, the storage device 806, the high-speed interface 808, the high-speed expansion ports 810, and the low-speed interface 812, are interconnected using various busses, and may be mounted on a common motherboard or in other manners as appropriate. The processor 802 can process instructions for execution within the computing device 800, including instructions stored in the memory 804 or on the storage device 806 to display graphical information for a GUI on an external input/output device, such as a display 816 coupled to the high-speed interface 808. In other implementations, multiple processors and/or multiple buses may be used, as appropriate, along with multiple memories and types of memory. Also, multiple computing devices may be connected, with each device providing portions of the necessary operations (e.g., as a server bank, a group of blade servers, or a multi-processor system).

The memory 804 stores information within the computing device 800. In some implementations, the memory 804 is a volatile memory unit or units. In some implementations, the memory 804 is a non-volatile memory unit or units. The memory 804 may also be another form of computer-readable medium, such as a magnetic or optical disk.

The storage device 806 is capable of providing mass storage for the computing device 800. In some implementations, the storage device 806 may be or contain a computer-readable medium, such as a floppy disk device, a hard disk device, an optical disk device, or a tape device, a flash memory or other similar solid state memory device, or an array of devices, including devices in a storage area network or other configurations. Instructions can be stored in an information carrier. The instructions, when executed by one or more processing devices (for example, processor 802), perform one or more methods, such as those described above. The instructions can also be stored by one or more storage devices such as computer- or machine-readable mediums (for example, the memory 804, the storage device 806, or memory on the processor 802).

The high-speed interface 808 manages bandwidth-intensive operations for the computing device 800, while the low-speed interface 812 manages lower bandwidth-intensive operations. Such allocation of functions is an example only. In some implementations, the high-speed interface 808 is coupled to the memory 804, the display 816 (e.g., through a graphics processor or accelerator), and to the high-speed expansion ports 810, which may accept various expansion cards (not shown). In the implementation, the low-speed interface 812 is coupled to the storage device 806 and the low-speed expansion port 814. The low-speed expansion port 814, which may include various communication ports (e.g., USB, Bluetooth®, Ethernet, wireless Ethernet) may be coupled to one or more input/output devices, such as a keyboard, a pointing device, a scanner, or a networking device such as a switch or router, e.g., through a network adapter.

The computing device 800 may be implemented in a number of different forms, as shown in the figure. For example, it may be implemented as a standard server 820, or multiple times in a group of such servers. In addition, it may be implemented in a personal computer such as a laptop computer 822. It may also be implemented as part of a rack server system 824. Alternatively, components from the computing device 800 may be combined with other components in a mobile device (not shown), such as a mobile computing device 850. Each of such devices may contain one or more of the computing device 800 and the mobile computing device 850, and an entire system may be made up of multiple computing devices communicating with each other.

The mobile computing device 850 includes a processor 852, a memory 864, an input/output device such as a display 854, a communication interface 866, and a transceiver 868, among other components. The mobile computing device 850 may also be provided with a storage device, such as a micro-drive or other device, to provide additional storage. Each of the processor 852, the memory 864, the display 854, the communication interface 866, and the transceiver 868, are interconnected using various buses, and several of the components may be mounted on a common motherboard or in other manners as appropriate.

The processor 852 can execute instructions within the mobile computing device 850, including instructions stored in the memory 864. The processor 852 may be implemented as a chipset of chips that include separate and multiple analog and digital processors. The processor 852 may provide, for example, for coordination of the other components of the mobile computing device 850, such as control of user interfaces, applications run by the mobile computing device 850, and wireless communication by the mobile computing device 850.

The processor 852 may communicate with a user through a control interface 858 and a display interface 856 coupled to the display 854. The display 854 may be, for example, a TFT (Thin-Film-Transistor Liquid Crystal Display) display or an OLED (Organic Light Emitting Diode) display, or other appropriate display technology. The display interface 856 may comprise appropriate circuitry for driving the display 854 to present graphical and other information to a user. The control interface 858 may receive commands from a user and convert them for submission to the processor 852. In addition, an external interface 862 may provide communication with the processor 852, so as to enable near area communication of the mobile computing device 850 with other devices. The external interface 862 may provide, for example, for wired communication in some implementations, or for wireless communication in other implementations, and multiple interfaces may also be used.

The memory 864 stores information within the mobile computing device 850. The memory 864 can be implemented as one or more of a computer-readable medium or media, a volatile memory unit or units, or a non-volatile memory unit or units. An expansion memory 874 may also be provided and connected to the mobile computing device 850 through an expansion interface 872, which may include, for example, a SIMM (Single In Line Memory Module) card interface. The expansion memory 874 may provide extra storage space for the mobile computing device 850, or may also store applications or other information for the mobile computing device 850. Specifically, the expansion memory 874 may include instructions to carry out or supplement the processes described above, and may include secure information also. Thus, for example, the expansion memory 874 may be provided as a security module for the mobile computing device 850, and may be programmed with instructions that permit secure use of the mobile computing device 850. In addition, secure applications may be provided via the SIMM cards, along with additional information, such as placing identifying information on the SIMM card in a non-hackable manner.

The memory may include, for example, flash memory and/or NVRAM memory (non-volatile random access memory), as discussed below. In some implementations, instructions are stored in an information carrier and, when executed by one or more processing devices (for example, processor 852), perform one or more methods, such as those described above. The instructions can also be stored by one or more storage devices, such as one or more computer- or machine-readable mediums (for example, the memory 864, the expansion memory 874, or memory on the processor 852). In some implementations, the instructions can be received in a propagated signal, for example, over the transceiver 868 or the external interface 862.

The mobile computing device 850 may communicate wirelessly through the communication interface 866, which may include digital signal processing circuitry where necessary. The communication interface 866 may provide for communications under various modes or protocols, such as GSM voice calls (Global System for Mobile communications), SMS (Short Message Service), EMS (Enhanced Messaging Service), or MMS messaging (Multimedia Messaging Service), CDMA (code division multiple access), TDMA (time division multiple access), PDC (Personal Digital Cellular), WCDMA (Wideband Code Division Multiple Access), CDMA2000, or GPRS (General Packet Radio Service), among others. Such communication may occur, for example, through the transceiver 868 using a radio-frequency. In addition, short-range communication may occur, such as using a Bluetooth®, Wi-Fi™, or other such transceiver (not shown). In addition, a GPS (Global Positioning System) receiver module 870 may provide additional navigation- and location-related wireless data to the mobile computing device 850, which may be used as appropriate by applications running on the mobile computing device 850.

The mobile computing device 850 may also communicate audibly using an audio codec 860, which may receive spoken information from a user and convert it to usable digital information. The audio codec 860 may likewise generate audible sound for a user, such as through a speaker, e.g., in a handset of the mobile computing device 850. Such sound may include sound from voice telephone calls, may include recorded sound (e.g., voice messages, music files, etc.) and may also include sound generated by applications operating on the mobile computing device 850.

The mobile computing device 850 may be implemented in a number of different forms, as shown in the figure. For example, it may be implemented as a cellular telephone 880. It may also be implemented as part of a smart-phone 882, personal digital assistant, or other similar mobile device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms machine-readable medium and computer-readable medium refer to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term machine-readable signal refers to any signal used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network (LAN), a wide area network (WAN), and the Internet.

The computing system can include clients and servers. A client and server are generally remote from each other and typically interact through a communication network. The relationship of client and server arises by virtue of computer programs running on the respective computers and having a client-server relationship to each other.

While the invention has been particularly shown and described with reference to specific preferred embodiments, it should be understood by those skilled in the art that various changes in form and detail may be made therein without departing from the spirit and scope of the invention as defined by the appended claims.

What is claimed is:

1. A method for quantifying two or more kinds of radionuclides present in a test sample, the method comprising:
    for each of a plurality of finite detected radioactive events in the test sample, obtaining, by a processor of a computing device, a measure of pulse shape, where the measure is a function of pulse intensity and pulse duration;
    sorting, by the processor, each of the finite detected radioactive events according to its measure of pulse shape into one of at least three categories using distinct first and second discriminator settings, where the event is identified as originating from a first kind of radionuclide if its measure of pulse shape has a value below the first discriminator setting, the event is identified as originating from a second kind of radionuclide if its measure of pulse shape has a value above the second discriminator setting, and the event is identified as indeterminate if its measure of pulse shape has a value between the first and second-discriminator settings; and
    displaying, by the processor, a measure of the first kind of radionuclide and a measure of the second kind of radionuclide.

2. The method of claim 1, wherein the two or more kinds of radionuclides comprise a beta emitter and an alpha emitter.

3. The method of claim 1, wherein each of the plurality of finite detected radioactive events has an associated signal of detected light intensity measured as a function of time by a liquid scintillation counter from which the measure of pulse shape is determined.

4. The method of claim 1, wherein the measure of pulse shape is or is a function of a measure of pulse or tail area divided by pulse amplitude.

5. The method of claim 1, wherein the event is identified as originating from a beta emitter if its measure of pulse shape has a value below the first discriminator setting and the event is identified as originating from an alpha emitter if its measure of pulse shape has a value above the second discriminator setting, where the first discriminator setting is lower than the second discriminator setting.

6. The method of claim 1, wherein the sorted events include a non-zero number of events in each of three categories—events originating from the first kind of radionuclide, events originating from the second kind of radionuclide, and indeterminate events.

7. The method of claim 1, wherein the measure of the first kind of radionuclide is or is a function of a sum of sorted events having a measure of pulse shape value below the first discriminator setting, and the measure of the second kind of radionuclide is or is a function of a sum of sorted events having a measure of pulse shape value above the second discriminator setting.

8. A method for applying discriminator settings in the quantification of radionuclides present in a test sample comprising at least a first and second radionuclide that are of different kinds, the method comprising:

receiving, by a processor of a computing device, data corresponding to a measure of pulse shape for each of a plurality of finite detected radioactive events in a first calibration sample comprising a first calibration radionuclide that is the same kind of emitter as and is or is similar to the first radionuclide in the test sample;

receiving, by the processor, data corresponding to a measure of pulse shape for each of a plurality of finite detected radioactive events in a second calibration sample comprising a second calibration radionuclide that is the same kind of emitter as and is or is similar to the second radionuclide in the test sample;

displaying, by the processor, a graphical representation of differentiated radioactive events corresponding to the first and second calibration samples as a function of corresponding measure of pulse shape;

displaying, by the processor, a graphical user interface element allowing adjustment of one or both of a first discriminator setting, and a second discriminator setting, and where an event is identified as originating from the first radionuclide if its measure of pulse shape has a value below the first discriminator setting, the event is identified as originating from the second radionuclide if its measure of pulse shape has a value above the second discriminator setting, and the event is identified as indeterminate if its measure of pulse shape has a value between the first and second discriminator settings;

receiving, by the processor, a selection by a user of a setting of the graphical user interface element defining the first and second discriminator settings;

determining and displaying, by the processor, a measure of spill and/or a measure of efficiency for each of the first and second calibration radionuclides given the user-selected setting of the graphical user interface element;

receiving, by the processor, an adjusted setting of the graphical user interface element corresponding to one or both of an adjusted first discriminator setting, and an adjusted second discriminator setting;

determining and displaying, by the processor, a measure of spill and/or a measure of efficiency for each of the first and second calibration radionuclides according to the adjusted setting of the graphical user interface element;

obtaining, by the processor, for each of a plurality of finite detected radioactive events in the test sample, a measure of pulse shape;

sorting, by the processor, each of the finite detected radioactive events in the test sample according to its measure of pulse shape using the adjusted setting of the graphical user interface element; and displaying, by the processor, a measure of the first radionuclide in the test sample and the second radionuclide in the test sample according to the adjusted setting of the graphical user interface element.

9. The method of claim 8, wherein each of the plurality of finite detected radioactive events in at least one of (i) the first calibration sample, (ii) the second calibration sample, and (iii) the test sample has an associated signal of detected light intensity measured as a function of time by a liquid scintillation counter from which the measure of pulse shape is determined.

10. The method of claim 8, wherein the first calibration sample does not comprise any radionuclide other than the first calibration radionuclide and/or wherein the second calibration sample does not comprise any radionuclide other than the second calibration radionuclide.

11. The method of claim 8, wherein the adjusted setting is a user-adjusted setting.

12. The method of claim 8, comprising sorting, by the processor, each of the finite detected radioactive events according to its measure of pulse shape into one of at least three categories using distinct first and second discriminator settings, where the event is identified as originating from a first kind of radionuclide if its measure of pulse shape has a value below the adjusted first discriminator setting, the event is identified as originating from a second kind of radionuclide if its measure of pulse shape has a value above the adjusted second discriminator setting, and the event is identified as indeterminate if its measure of pulse shape has a value between the adjusted first and the adjusted second discriminator settings.

13. A method for automatically optimizing discriminator settings in the quantification of radionuclides present in a test sample comprising at least a first and second radionuclide that are of different kinds, the method comprising:

receiving, by a processor of a computing device, data corresponding to a measure of pulse shape for each of a plurality of finite detected radioactive events in a first calibration sample comprising a first calibration radionuclide that is the same kind of emitter as and is or is similar to the first radionuclide in the test sample;

receiving, by the processor, data corresponding to a measure of pulse shape for each of a plurality of finite detected radioactive events in a second calibration sample comprising a second calibration radionuclide that is the same kind of emitter as and is or is similar to the second radionuclide in the test sample;

for each of a plurality of settings of both of a first discriminator setting and a second discriminator setting different from the first discriminator setting, determining, by the processor, for each of the first and second calibration radionuclides: (i) a measure of spill and (ii) a measure of efficiency, where an event is identified as originating from the first calibration radionuclide if its measure of pulse shape has a value below the first discriminator setting, the event is identified as originating from the second calibration radionuclide if its measure of pulse shape has a value above the second discriminator setting, and the event is identified as indeterminate if its measure of pulse shape has a value between the first and second discriminator settings;

computing, by the processor, a figure of merit (FOM) corresponding to each of the plurality of settings of the first discriminator setting and the second discriminator setting, where the FOM is a function of spill and efficiency;

determining, by the processor, an accepted setting of the first discriminator setting and the second discriminator setting that produces an acceptably high FOM;

obtaining, by the processor, for each of a plurality of finite detected radioactive events in the test sample, a measure of pulse shape;

sorting, by the processor, each of the finite detected radioactive events in the test sample according to its measure of pulse shape using the accepted setting of the first discriminator setting and the second discriminator setting; and displaying, by the processor, a measure of the first radionuclide in the test sample and the second radionuclide in the test sample according to the accepted setting of the first discriminator setting and the second discriminator setting.

14. The method of claim 13, wherein each of the plurality of finite detected radioactive events in at least one of (i) the first calibration sample, (ii) the second calibration sample, and (iii) the test sample has an associated signal of detected light intensity measured as a function of time by a liquid scintillation counter from which the measure of pulse shape is determined.

15. The method of claim 13, wherein the first calibration sample does not comprise any radionuclide other than the first calibration radionuclide and/or wherein the second calibration sample does not comprise any radionuclide other than the second calibration radionuclide.

16. The method of claim 13, wherein the accepted setting of the first discriminator setting and the second discriminator setting is an optimized setting that maximizes the FOM.

17. The method of claim 13, comprising sorting, by the processor, each of the finite detected radioactive events according to its measure of pulse shape into one of at least three categories using distinct first and second discriminator settings, where the event is identified as originating from a first kind of radionuclide if its measure of pulse shape has a value below the accepted first discriminator setting, the event is identified as originating from a second kind of radionuclide if its measure of pulse shape has a value above the accepted second discriminator setting, and the event is identified as indeterminate if its measure of pulse shape has a value between the accepted first and the accepted second discriminator settings.

18. A radiation detection system for quantifying two or more kinds of radionuclides present in a test sample, the system comprising:

a detector for producing a pulse signal corresponding to each of a plurality of detected radioactive events in a test sample;

a processor; and a memory having instructions stored thereon, wherein the instructions, when executed by the processor, cause the processor to:

for each of the plurality of detected radioactive events in the test sample, obtain a measure of pulse shape from the corresponding pulse signal, where the measure is a function of pulse intensity and pulse duration;

sort each of the detected radioactive events according to its measure of pulse shape into one of at least three categories using distinct first and second discriminator settings, where the event is identified as originating from a first kind of radionuclide if its measure of pulse shape has a value below the first discriminator setting, the event is identified as originating from a second kind of radionuclide if its measure of pulse shape has a value above the second discriminator setting, and the event is identified as indeterminate if its measure of pulse shape has a value between the first and second discriminator settings; and display a measure of the first kind of radionuclide and a measure of the second kind of radionuclide.

19. The system of claim 18, wherein the detector is a liquid scintillation counter comprising one or more photomultiplier tubes.

20. The system of claim 18, wherein the test sample is a cocktail comprising a sample material, a solvent for the sample material, and a scintillator, and the sample material comprises a radionuclide that undergoes radioactive decay, whereby the decay energy causes excitation of the scintillator and release of UV light that is detected.

21. The system of claim 20, wherein the scintillator is a fluor.

22. The system of claim 18, wherein the corresponding pulse signal is a measure of detected light intensity as a function of time.

* * * * *